(12) United States Patent
Chang et al.

(10) Patent No.: US 7,163,795 B2
(45) Date of Patent: Jan. 16, 2007

(54) METHODS AND COMPOSITIONS FOR PEARL OYSTER CULTIVATION

(75) Inventors: Fang-Tseh (Frank) Chang, Belmont, CA (US); Hung Li, Taipei (TW); Hsiu Mei Hsieh-Li, Taipei (TW)

(73) Assignee: Changene, Inc., Moffett Field, CA (US)

( * ) Notice: Subject to any disclaimer, the term of this patent is extended or adjusted under 35 U.S.C. 154(b) by 76 days.

(21) Appl. No.: 11/049,348

(22) Filed: Feb. 1, 2005

(65) Prior Publication Data

US 2005/0282183 A1 Dec. 22, 2005

Related U.S. Application Data

(63) Continuation of application No. 10/086,510, filed on Feb. 27, 2002, now abandoned.

(60) Provisional application No. 60/310,070, filed on Aug. 2, 2001.

(51) Int. Cl.
*C12Q 1/68* (2006.01)
*C12N 1/21* (2006.01)
*C12N 5/10* (2006.01)
*C07H 21/04* (2006.01)

(52) U.S. Cl. ........................ 435/6; 435/252.3; 435/325; 536/23.5

(58) Field of Classification Search .................... None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,736,866 A | 4/1988 | Leder et al. | |
| 4,754,065 A | 6/1988 | Levenson et al. | |
| 4,800,159 A | 1/1989 | Mullis et al. | |
| 4,870,009 A | 9/1989 | Evans et al. | |
| 4,873,191 A | 10/1989 | Wagner et al. | |
| 5,124,426 A | 6/1992 | Primeaux, II et al. | |
| 5,451,514 A * | 9/1995 | Boudet et al. | 800/286 |
| 5,510,270 A | 4/1996 | Fodor et al. | |
| 5,556,752 A | 9/1996 | Lockhart et al. | |
| 5,578,832 A | 11/1996 | Trulson et al. | |
| 5,723,315 A | 3/1998 | Jacobs et al. | |
| 5,968,772 A | 10/1999 | Matsushiro | |
| 6,001,592 A | 12/1999 | Nakashima et al. | |
| 6,341,580 B1 | 1/2002 | Langdon | |

FOREIGN PATENT DOCUMENTS

| | | | |
|---|---|---|---|
| WO | WO-03/020019 A2 | 3/2003 | |
| WO | WO-03/020019 A3 | 3/2003 | |

OTHER PUBLICATIONS

Genbank locus 114661 showing 38-nt fragment in the alignment of SEQ ID No. 1 with SEQ ID No.19 form USP 5451514.*
Genbank locus AF061570 showing 37-nt fragment in alignment with instant SEQ ID No. 1.*
Genbank locus AB032613, two sequences showing fragments greater than 25-nt.*
Blanchard, A.P. et al. (1996). "High-Density Oligonucleotide Arrays," *Biosensors & Bioelectronics* 11(6/7):687-690.
DeRisi, J. et al. (1996). "Use of a cDNA Microarray to Analyse Gene Expression Patterns in Human Cancer," *Nature Genetics* 14:457-460.
Fodor, S. et al. (1991). "Light-Directed, Spatially Addressable Parallel Chemical Synthesis," *Science* 251:767-773.
GenBank Accession No. AB032613, created Dec. 27, 2005, located at <http://www.ncbi.nlm.nih.gov/entrez/viewer.fcgi?db=nuccore &val=6899835>, last visited on Mar. 15, 2006, two pages.
GenBank Accession No. AF061570, created May 9, 1998, located at <http://www.ncbi.nlm.nih.gov/entrez/viewer.fcgi?db=nuccore &val=3126867>, last visited on Mar. 15, 2006, two pages.
International Search Report mailed on Oct. 31, 2003, for PCT Application No. PCT/US02/23512 filed Jul. 23, 2002, 7 pages.
Khrapko, K.R. et al. (1991). "A Method for DNA Sequencing by Hybridization with Oligonucleotide Matrix," *DNA Sequence-J. DNA Sequencing and Mapping* 1:375-388.
Komachi, K. et al. (1994). "The WD Repeats of Tup1 Interact with the Homeo Domain Protein α2," *Genes & Development* 8:2857-2867.
Kono, M. et al. (2000). "Molecular Mechanism of the Nacreous Layer Formation in *Pinctada maxima*," *Biochemical and Biophysical Research Communications* 269(1):213-218.
Lockhart, D.J. et al. (1996). "Expression Monitoring by Hybridization to High-Density Oligonucleotide Arrays," *Nature Biotechnology* 14:1675-1680.
Marshall, A. and Hodgson, J. (1998). "DNA chips: An Array of Possibilities," *Nature Biotechnoogy* 16:27-31.
Maskos,U. and Southern, E.M. (1992). "Oligonucleotide Hybridisations on Glass Supports: a Novel Linker for Oligonucleotide Synthesis and Hybridisation Properties of Oligonucleotides Synthesised in situ," *Nucleic Acids Research* 20(7):1679-1684.
Matson, R.S. et al. (1995) "Biopolymer Synthesis on Polypropylene Supports: Oligonucleotide Arrays," *Analytical Biochemistry* 224(1):110-116.
Merrifield, R.B. (1963). "Solid Phase Peptide Synthesis. I. The Synthesis of a Tetrapeptide," *J. Am. Chem. Soc.* 85:2149-2154.
Pease, A.C. et al. (1994). "Light-Generated Oligonucleotide Arrays for Rapid DNA Sequence Analysis," *Proc. Natl. Acad. Sci. USA* 91:5022-5026.

(Continued)

*Primary Examiner*—Robert A. Wax
(74) *Attorney, Agent, or Firm*—Morrison & Foerster LLP

(57) ABSTRACT

The invention provides methods and compositions useful in pearl oyster cultivation. Polynucleotide and polypeptides relating to the nacre gene of *Pinctada margaritifera* are provided. Antibodies related to these polypeptides, and compositions comprising polynucleotides, polypeptides and/or antibodies of the invention are also provided. The invention provides methods of using these polynucleotides, polypeptides and antibodies, including methods related to pearl oyster cultivation. Arrays comprising polynucleotides, polypeptides and/or antibodies of the invention are also provided.

24 Claims, No Drawings

OTHER PUBLICATIONS

Posnett, D.N. et al. (1988). "A Novel Method for Producing Anti-Peptide Antibodies," *Journal of Bioogical Chemistry* 263(4):1719-1725.

Ramsay, G. (1998). "DNA Chips: State-of-the Art," *Nature Biotechnology* 16:40-44.

Schena, M. et al. (1995). "Quantitative Monitoring of Gene Expression Patterns with a Complementary DNA Microarray," *Science* 270:467-470.

Schena, M. et al. (1996). "Parallel Human Genome Analysis: Microarray-Based Expression Monitoring of 1000 Genes," *Proc. Natl. Acad. Sci. USA* 93:10614-10619.

Shalon, D. et al. (1996). "A DNA Microarray System for Analyzing Complex DNA Samples Using Two-Color Fluorescent Probe Hybridization," *Genome Research* 6:639-645.

Smith, T.F. and Waterman, M.S. (1981). "Comparison of Biosequences," *Advances in Applied Mathematics* 2:482-489.

Spira, G. et al.(1984). "The Identification of Monoclonal Class Switch Variants by Sib Selection and an ELISA Assay," *Journal of Immunological Methods* 74:307-315.

Steplewski, Z. et al. (1985). "Isolation and Characterization of Anti-Monosialoganglioside Monoclonal Antibody 19-9 Class-Switch Variants," *Proc. Natl. Acad. Sci. USA* 82:8653-8657.

Tam, J.P. (1989). "High-Density Multiple Antigen-Peptide System for Preparation of Antipeptide Antibodies," *Methods of Enymology* 168:7-15.

\* cited by examiner

METHODS AND COMPOSITIONS FOR PEARL OYSTER CULTIVATION

CROSS-REFERENCE TO RELATED APPLICATIONS

This application is a continuation application of U.S. patent application Ser. No. 10/086,510, filed on Feb. 27, 2002, now abandoned which claims the benefit of U.S. Provisional Application No. 60/310,070, filed Aug. 2,2001.

TECHNICAL FIELD

The invention relates to pearl oyster cultivation. In particular, it relates to polynucleotides and polypeptides of the nacre gene of *Pinctada margaritifera*, and methods of using these polynucleotides and polypeptides in pearl oyster cultivation.

BACKGROUND ART

Traditional methods of pearl oyster cultivation tend to be inefficient. For example, there is no guarantee that each oyster that is cultivated would produce a pearl at all, let alone a pearl possessing a desired characteristic. A pearl is produced through about 1 to 3 years of cultivation of the pearl oyster following transplantation into the pearl oyster gonad of a nucleus made of, for example, a piece of a shell, along with a piece of mantle tissue. Many factors combine to vary the results of pearl oyster cultivation, and consequently usually only a portion of the pearl crop is of acceptable quality. For example, an oyster may get weak from overcrowding or a lack of sufficient plankton in the water in which it is being cultivated. Hitherto, conditions agreeable for a pearl oyster with respect to pearl formation are generally determined through a "hit-or-miss" approach.

The product of the nacre gene is an acidic protein (nacrein) implicated in pearl formation. Nacrein has a calcium ion binding activity. A pearl is an aggregation of calcium carbonate, among other components, on an organic matrix.

Inefficiency in the traditional methods of cultivation is due in large part to lack of understanding of the pearl formation process at the molecular level. This lack of understanding, in turn, is due in large part to lack of access to the genetic information underlying the pearl formation process. Sequences of a limited number of genes of certain species of pearl oyster have been disclosed. See, for example, U.S. Pat. Nos. 5,968,772 and 6,001,592.

The present invention addresses these problems by providing polynucleotides and polypeptides from the nacre gene of *Pinctada margaritifera*. These polynucleotides and polypeptides can be used in a variety of ways, including in improved methods of pearl oyster cultivation.

SUMMARY OF THE INVENTION

This invention provides *Pinctada margaritifera* nacre gene polynucleotide sequences, nacrein polypeptides encoded by these sequences, antibodies that bind to these polypeptides, compositions comprising any of the above, as well as methods using the polynucleotides, polypeptides, and/or antibodies. Arrays comprising these polynucleotides, polypeptides and/or antibodies are also provided by the invention.

Accordingly, in one aspect, the invention provides an isolated polynucleotide comprising a sequence encoding a nacrein or nacrein-related polypeptide, or fragment thereof, preferably from the *Pinctada margaritifera* species. In one embodiment, the invention provides an isolated polynucleotide comprising: a) a polynucleotide having the sequence as shown in SEQ ID NO:1, or its complement; or b) a fragment of said polynucleotide wherein said fragment is: i) at least 10, 15, 20, 25, 30, 35, 40, 45 or 50 nucleotides in length; and ii) does not correspond identically in its entirety to any portion of the sequence shown in SEQ ID NOs:2 or 3 or any other known polynucleotide; or c) a polynucleotide that selectively hybridizes to the sequence of SEQ ID NO:1, or said fragment, relative to a known polynucleotide. In one embodiment, said polynucleotide that selectively hybridizes to the sequence of SEQ ID NO:1, or said fragment, relative to a known polynucleotide, hybridizes under intermediate stringency conditions. In another embodiment, said polynucleotide that selectively hybridizes to the sequence of SEQ ID NO:1, or said fragment, relative to a known polynucleotide, hybridizes under high stringency conditions. In one embodiment, said polynucleotide comprises the sequence as shown in SEQ ID NO:1, or its complement, or said fragment thereof. In yet another embodiment, the invention provides polynucleotides comprising a sequence with at least 40%, at least 50%, preferably at least 60%, more preferably at least 70%, even more preferably at least 80%, more preferably at least 90%, most preferably at least 95% sequence identity with the sequence depicted in SEQ ID NO:1, wherein said sequence does not correspond identically in its entirety to any portion of the sequence shown in SEQ ID NOs:2 or 3, or any other known polynucleotide. In another embodiment, said polynucleotide consists essentially of the sequence shown in SEQ ID NO:1, or its complement, or a fragment thereof. In some embodiments, any of these polynucleotides can be at least 450, preferably at least 500, more preferably at least 600, even more preferably at least 1000, still more preferably at least 2000, more preferably at least 3000, most preferably at least 5000 nucleotides in length. In some embodiments, any of these polynucleotides can be up to about 450, preferably up to about 500, more preferably up to about 600, even more preferably up to about 1000, still more preferably up to about 2000, more preferably up to about 3000, and most preferably up to about 5000 nucleotides in length. In some embodiments, any of these polynucleotides is between about 450 and about 5000, more preferably between about 500 and about 3000, even more preferably between about 600 and about 2000, and most preferably between about 1000 and about 2000 nucleotides in length. In some embodiments, these polynucleotides comprise a genomic sequence. In some embodiments, the genomic sequence comprises a region of at least 50, 100, 150, 200, 250, 300, 400, or 500 contiguous nucleotides, wherein said region is contained in the sequence depicted in SEQ ID NO:1, wherein said region does not correspond identically in its entirety to any portion of the sequence shown in SEQ ID NOs:2 or 3, or any other known polynucleotide. In some embodiments, the genomic sequence comprises a region of at least 50, 100, 150, 200, 250, 300, 400, or 500 contiguous nucleotides, with the region having at least 40%, at least 50%, more preferably at least 60%, even more preferably at least 70%, still more preferably at least 80%, and most preferably at least 90% sequence identity with a sequence depicted within SEQ ID NO:1, wherein said sequence does not correspond identically in its entirety to any portion of the sequence shown in SEQ ID NOs:2 or 3, or any other known polynucleotide.

In one embodiment, the invention provides polynucleotides comprising a sequence with at least 70%, more preferably at least 80%, most preferably at least 90%, most preferably at least 95% sequence identity with the sequence depicted in SEQ ID NO:1, wherein said sequence does not correspond identically in its entirety to any portion of the sequence shown in SEQ ID NO:2, or any other known polynucleotide. In some embodiments, any of these polynucleotides can be at least 450, preferably at least 500, more preferably at least 600, even more preferably at least 1000, still more preferably at least 2000, more preferably at least 3000, most preferably at least 5000 nucleotides in length. In some embodiments, any of these polynucleotides can be up to about 450, preferably up to about 500, more preferably up to about 600, even more preferably up to about 1000, still more preferably up to about 2000, more preferably up to about 3000, and most preferably up to about 5000 nucleotides in length. In some embodiments, any of these polynucleotides is between about 450 and about 5000, more preferably between about 500 and about 3000 nucleotides, even more preferably between about 600 and about 2000, and most preferably between about 1000 and about 2000 nucleotides in length. In some embodiments, these polynucleotides comprise a genomic sequence. In some embodiments, the genomic sequence comprises at region of at least 50, 100, 150, 200, 250, 300, 400, or 500 contiguous nucleotides, with the region having at least 70%, at least 80%, more preferably at least 90%, even more preferably at least 70%, still more preferably at least 80%, and most preferably at least 95% sequence identity with a sequence depicted within SEQ ID NO:1, wherein said sequence does not correspond identically in its entirety to any portion of the sequence shown in SEQ ID NOs:2, or any other known polynucleotide.

In one embodiment, the invention provides polynucleotides comprising a sequence with at least 90%, more preferably at least 95%, most preferably at least 98%, most preferably at least 99% sequence identity with the sequence depicted in SEQ ID NO:1, wherein said sequence does not correspond identically in its entirety to any portion of any known polynucleotide. In some embodiments, any of these polynucleotides can be at least 450, preferably at least 500, more preferably at least 600, even more preferably at least 1000, still more preferably at least 2000, more preferably at least 3000, most preferably at least 5000 nucleotides in length. In some embodiments, any of these polynucleotides can be up to about 450, preferably up to about 500, more preferably up to about 600, even more preferably up to about 1000, still more preferably up to about 2000, more preferably up to about 3000, and most preferably up to about 5000 nucleotides in length. In some embodiments, any of these polynucleotides is between about 450 and about 5000, more preferably between about 500 and about 3000 nucleotides, even more preferably between about 600 and about 2000, and most preferably between about 1000 and about 2000 nucleotides in length. In some embodiments, these polynucleotides comprise a genomic sequence. In some embodiments, the genomic sequence comprises at region of at least 50, 100, 150, 200, 250, 300, 400, or 500 contiguous nucleotides, with the region having at least 90%, at least 95%, more preferably at least 98%, even more preferably at least 99% sequence identity with a sequence depicted within SEQ ID NO:1, wherein said sequence does not correspond identically in its entirety to any portion of any known polynucleotide.

In one aspect, the invention provides fragments of any of the polynucleotides described herein. These fragments are preferably at least 10, 12, 15, 20, 25, 30, 35, 40, 45 or 50 nucleotides in length. In some embodiments, a fragment comprises a sequence with preferably at least 80%, more preferably at least 85%, even more preferably at least 90%, and most preferably at least 95% sequence identity with a sequence depicted in SEQ ID NO:1, wherein said sequence does not correspond identically in its entirety to any portion of the sequence shown in SEQ ID NOs:2 or 3, or any other known polynucleotide.

In some embodiments, the polynucleotides of the invention, complements of these polynucleotides, or fragments of the polynucleotides further comprise a detectable label.

In some embodiments, the polynucleotides of the invention, complements of these polynucleotides, or fragments of the polynucleotides are attached to a solid support. For example, the invention provides arrays and microarrays comprising polynucleotides, polypeptides, and/or antibodies of the invention.

In one aspect, the invention provides a host cell comprising an isolated polynucleotide of the present invention. A host cell can be of any species. A host cell is preferably of bacterial, molluscan (for example, oyster, preferably pearl oyster) or mammalian in origin.

In another aspect, the invention provides isolated polypeptides encoded by any of the polynucleotides of the present invention as described herein. In one embodiment, the invention provides an isolated polypeptide comprising: a) a polypeptide having the sequence as shown in SEQ ID NO:4; or b) a fragment of said polypeptide wherein said fragment is: i) at least 10, 15, 20, 25, 30, 35, 40, 45, 50, 75, 100, 150, 200 amino acids in length; and ii) does not correspond identically in its entirety to any portion of the sequence shown in SEQ ID NOs:5 or 6 or any other known polypeptide. In yet another embodiment, the invention provides polypeptides comprising a sequence with at least 50%, preferably at least 60%, more preferably at least 70%, even more preferably at least 80%, more preferably at least 90%, most preferably at least 95% sequence identity with the sequence depicted in SEQ ID NO:4, wherein said sequence does not correspond identically in its entirety to any portion of the sequence shown in SEQ ID NOs:5 or 6, or any other known polypeptide.

In one aspect, the invention provides fragments of any of the polypeptides described herein. These fragments are preferably at least 10, 15, 20, 25, 30, 35, 40, 45, 50, 75, 100, 150, 200 amino acids in length. In some embodiments, a fragment comprises a sequence with preferably at least 80%, more preferably at least 85%, even more preferably at least 90%, and most preferably at least 95% sequence identity with a sequence depicted in SEQ ID NO:4, wherein said sequence does not correspond identically in its entirety to any portion of the sequence shown in SEQ ID NOs:5 or 6, or any other known polypeptide.

In one aspect, the invention provides a polypeptide comprising amino acids 81–194 of SEQ ID NO:4. In another embodiment, the invention provides a polypeptide comprising amino acids 520–609 of SEQ ID NO:4. In a still further embodiment, the invention provides a polypeptide comprising amino acids 81–194 and 520–609 of SEQ ID NO:4. In some embodiments, the invention provides a polypeptide comprising a region comprising at least 5, more preferably at least 10, even more preferably at least 15, still more preferably at least 20, and most preferably at least 30 contiguous amino acids, with the region having at least 50%, more preferably at least 60%, even more preferably at least 70%, still more preferably at least 80%, and most preferably at least 90% sequence identity with a sequence depicted within the sequence from amino acids 81–194 or 520–609 of SEQ ID NO:4, wherein said sequence does not correspond identically in its entirety to any portion of the sequence shown in SEQ ID NOs:5 or 6, or any other known polypeptide. In one embodiment, the invention provides a polypeptide comprising an amino acid sequence with preferably at least 50%, more preferably at least 60%, even more preferably at least 70%, still more preferably at least 80%, and most preferably at least 90% sequence identity with the sequence from amino acids 81–194 or 520–609 of SEQ ID NO:4, wherein said sequence does not correspond identically in its entirety to any portion of the sequence shown in SEQ ID NOs:5 or 6, or any other known polypeptide.

In yet another aspect, the invention provides isolated polynucleotides comprising a sequence encoding any of the polypeptides of the present invention. In one embodiment, these isolated polynucleotides comprise a genomic sequence. In one embodiment, these isolated polynucleotides comprise an intronic sequence. In one embodiment, these isolated polynucleotides comprise a genomic sequence of *Pinctada margaritifera* origin. In another embodiment, these isolated polynucleotides comprise an intronic sequence of *Pinctada margaritifera* origin. These polynucleotides can be of any length, and in one embodiment are preferably at least about 1000, 2000, 3000, 4000, 5000 or 6000 nucleotides in length. In another embodiment, these polynucleotides are up to about 1000, preferably up to about 2000, more preferably up to about 3000, even more preferably up to about 4000, more preferably up to about 5000, most preferably up to about 6000 nucleotides in length. In yet another embodiment, these polynucleotides are between about 1000 and about 6000, preferably between about 2000 and about 5000, more preferably between about 3000 and about 4000 nucleotides in length. In one embodiment, the invention provides isolated polynucleotides encoding nacrein protein, or fragments thereof, of *Pinctada margaritifera*. In some embodiments, the isolated polynucleotides encoding nacrein protein, or fragments thereof, comprise a sequence contained in SEQ ID NO:1. In some of these embodiments, said sequence contained in SEQ ID NO:1 comprises a region containing at least 50, 100, 150, 200, 250, 300, 400, 500, 750, 1000, 1500 or 2000 contiguous nucleotides depicted in SEQ ID NO:1. In some embodiments, these polynucleotides are between 1000 to 6000 nucleotides in length. In other embodiments, these polynucleotides are between 1000 to 2000 nucleotides in length.

In another aspect, the invention provides polynucleotides comprising a sequence from the nacre gene of *Pinctada margaritifera* and a sequence from another gene. Preferably, said another gene is a nacre gene from a different oyster species. In one embodiment, a polynucleotide of the invention comprises a sequence from the nacre gene of *Pinctada margaritifera* and a sequence from the nacre gene of *Pinctada maxima* (for example, a sequence contained in the sequence depicted in SEQ ID NO:2). In another embodiment, a polynucleotide of the invention comprises a sequence from the nacre gene of *Pinctada margaritifera*, a sequence from the nacre gene of *Pinctada maxima* (for example, a sequence contained in the sequence depicted in SEQ ID NO:2) and a sequence from the nacre gene of *Pinctada fucata* (for example, a sequence contained in the sequence depicted in SEQ ID NO:3). In another embodiment, a polynucleotide of the invention comprises a sequence from the nacre gene of *Pinctada margaritifera* and a sequence from the nacre gene of *Pinctada fucata* (for example, a sequence contained in the sequence depicted in SEQ ID NO:3).

In another aspect, the invention provides an isolated polynucleotide comprising a region of at least 20, more preferably at least 50, even more preferably at least 75, and most preferably at least 100 contiguous nucleotides, with the region having at least 80%, preferably at least 85%, more preferably at least 90%, most preferably at least 95% sequence identity with a sequence depicted in SEQ ID NO:1, wherein said region does not correspond identically in its entirety to any portion of the sequence shown in SEQ ID NOs:2 or 3, or any other known polynucleotide. In other embodiments, the invention provides an isolated polynucleotide comprising a region of at least 20, 50, 75, or 100 contiguous nucleotides, with the region able to hybridize under moderate or stringent conditions to the sequence depicted in SEQ ID NO:1, wherein said region does not correspond identically in its entirety to any portion of the sequence shown in SEQ ID NOs:2 or 3, or any other known polynucleotide.

In one aspect, the invention provides methods for using polynucleotides and/or polypeptides (including antibodies, and fragment thereof), for example in aspects of cultivation of pearl oyster, preferably *Pinctada margaritifera*.

Accordingly, in one aspect, the invention provides methods of determining a condition that permits pearl formation, said method comprising cultivating a pearl oyster under a condition of interest and detecting expression of nacre gene of the oyster by contacting a sample from the oyster with a polynucleotide of the present invention (generally under conditions that permit detection of expression of the nacre gene using the said polynucleotide), whereby detection of said expression indicates that said condition of interest permits pearl formation. A condition of interest includes, but is not limited to, water conditions (such as temperature, ionic strength, chemical composition, depth), mantle tissue transplantation technique, duration of culture, physical characteristics of an oyster, and age of an oyster. Detection of expression can be achieved by any of a variety of techniques known in the art, including, for example, nucleic acid hybridization and/or nucleic acid amplification. The pearl oyster used in the methods of the invention can be of any species. In one embodiment, the pearl oyster used in methods of the invention is of the species *Pinctada margaritifera*. The sample in which nacre gene expression is to be detected generally comprises nucleic acid molecules, preferably RNA. The sample can be from any part of the oyster in which the nacre gene is known or suspected to be expressed. Preferably, the sample is from mantle tissue.

In one aspect, the invention includes cloning vectors, expression vectors, host cells, and compositions comprising any of the above polynucleotides.

In another aspect, the invention includes compositions comprising any of the polynucleotides and/or polypeptides (including antibodies) of the invention.

In still another aspect, the invention provides isolated (generally purified) antibodies or antigen binding fragments thereof, that bind to a polypeptide of the invention, or fragment thereof, as described herein. These antibodies are generally and preferably capable of specifically binding to a polypeptide, or fragment thereof, of the invention. In one embodiment, an antibody of the invention is a monoclonal antibody. In another embodiment, an antibody of the invention is a polyclonal antibody. In yet another embodiment, an antibody of the invention is provided as an antiserum. In still another embodiment, an antibody of the invention is provided as ascites fluid.

In one embodiment, the invention provides an isolated antibody that binds to a polypeptide, or fragment thereof, of the invention, said antibody made by a method comprising: (a) immunizing a host animal with a composition comprising said polypeptide, or fragment thereof; and (b) collecting cells from said host expressing antibodies against the polypeptide, or fragment thereof.

In another embodiment, the invention provides an isolated antibody that binds to a polypeptide or fragment thereof, of the invention, said antibody made by a method comprising: (a) providing a cell line producing an antibody, wherein said antibody binds to said polypeptide, or fragment thereof; and (b) culturing said cell line under conditions wherein said antibodies are produced.

In one aspect, the invention provides methods of determining a condition that permits pearl formation, said method comprising: a) cultivating a pearl oyster under a condition of interest; and b) detecting expression of nacre gene of the oyster by contacting a sample from the oyster with an antibody of the present invention (generally under conditions that permit formation of a stable antibody-antigen complex), whereby detection of said expression indicates that said condition of interest permits pearl formation. Detection of expression can be achieved by any of a variety of techniques known in the art. The pearl oyster used in the methods of the invention can be of any species. In one embodiment, the pearl oyster used in methods of the invention is of the species *Pinctada margaritifera*. The sample in which nacre gene expression is to be detected generally comprises polypeptides, preferably nacrein protein and/or fragments thereof. The sample can be from any part of the oyster in which the nacre gene is known or suspected to be expressed. Preferably, the sample is from mantle tissue.

In yet another aspect, the invention provides methods of detecting a nacrein-expressing oyster, said method comprising: (a) contacting a sample from said oyster with a polynucleotide, or fragment thereof, described herein; and (b) detecting hybridization of said polynucleotide to the sample. Detection of expression can be achieved by any of a variety of techniques known in the art. The pearl oyster used in the methods of the invention can be of any species. In one embodiment, the pearl oyster used in methods of the invention is of the species *Pinctada margaritifera*. The sample in which nacre gene expression is to be detected generally comprises nucleic acids, preferably RNA. The sample can be from any part of the oyster in which the nacre gene is known or suspected to be expressed. Preferably, the sample is from mantle tissue.

In yet another aspect, the invention provides methods of detecting a nacrein-expressing oyster, said method comprising: (a) contacting a sample from said oyster with an antibody described herein (generally under conditions that permit formation of a stable antibody-antigen complex); and (b) detecting binding of said antibody (for example, detecting an antibody-antigen complex) to the sample. Detection of expression can be achieved by any of a variety of techniques known in the art. The pearl oyster used in the methods of the invention can be of any species. In one embodiment, the pearl oyster used in methods of the invention is of the species *Pinctada margaritifera*. The sample in which nacre gene expression is to be detected generally comprises polypeptides, preferably nacrein protein and/or fragments thereof. The sample can be from any part of the oyster in which the nacre gene is known or suspected to be expressed. Preferably, the sample is from mantle tissue.

In still another aspect, the invention provides methods of quantifying nacre gene expression in a sample, said method comprising: (a) contacting said sample with a polynucleotide described herein (generally under conditions that permit nucleic acid hybridization); (b) detecting hybridization of said polynucleotide to said sample; (c) comparing the amount of the hybridization of step (b) with the amount of hybridization of said polynucleotide to a reference polynucleotide. A reference polynucleotide can be any polynucleotide that permits quantification of nacre gene expression according to the method of the invention. A reference polynucleotide may or may not comprise a sequence related to the nacre gene. If the amount of a reference polynucleotide is known, comparison of the amount of hybridization of the polynucleotide of the invention to the sample and to the reference polynucleotide would permit quantification of nacre gene expression in the sample. The sample can be from any source suspected or known to contain nucleic acids reflective of nacre gene expression. In one embodiment, the sample is obtained from a pearl oyster, preferably *Pinctada margaritifera*.

In another aspect, the invention provides methods of quantifying nacrein in a sample, said method comprising: (a) contacting said sample with an antibody of the invention as described herein (under conditions that permit formation of a stable antibody-antigen complex); (b) detecting binding of said antibody to said sample (for example, detecting an antibody-antigen complex); (c) comparing the amount of the binding of step (b) with the amount of binding of said antibody to a reference polypeptide. A reference polypeptide can be any polypeptide that permits quantification of nacre gene expression according to the method of the invention. A reference polypeptide may or may not comprise a sequence related to the nacrein protein. If the amount of a reference polypeptide is known, comparison of the amount of binding of the polypeptide of the invention to the sample and to the reference polypeptide would permit quantification of nacrein in the sample. The sample can be from any source suspected or known to contain the nacrein protein, or fragments thereof, reflective of nacre gene expression. In one embodiment, the sample is obtained from a pearl oyster, preferably *Pinctada margaritifera*.

In another aspect, the invention provides kits for detection or quantification of (a) a polynucleotide comprising a nacre gene sequence from pearl oyster (preferably *Pinctada margaritifera*); or (b) a polypeptide comprising an amino acid sequence of a nacrein protein, or fragment thereof, from pearl oyster (preferably *Pinctada margaritifera*); or (c) an anti-*Pinctada margaritifera* nacrein (or fragment thereof) antibody in a biological sample. These kits contain (a) a polynucleotide of the invention; (b) an antibody of the invention; and/or (c) a polypeptide of the invention, respectively.

In still another aspect, the invention provides transgenic organisms comprising a polynucleotide described herein. Preferably, the transgenic organism is molluscan, preferably a pearl oyster, preferably of the *Pinctada margaritifera* species. In some embodiments, the transgenic organism is mammalian, for example mouse or rat.

MODES FOR CARRYING OUT THE INVENTION

We have cloned polynucleotides encoding sequences of the nacre gene from *Pinctada margaritifera* and have discovered that these polynucleotides, and their corresponding polypeptides (and antibodies), can be used in various aspects of pearl oyster cultivation. The discovery of these polynucleotides, polypeptides and antibodies greatly benefits efforts to increase efficiency in the pearl oyster cultivation industry. These polynucleotides, polypeptides and antibodies are useful, for example, in determining suitable and/or optimal conditions for cultivating pearl oysters, thus reducing much of the uncertainty presently existing in this industry. They can also be used in the formation of pearls, and/or components of pearls, thus reducing the costs of such efforts.

Accordingly, the invention provides nacre polynucleotide sequences, including polynucleotides encoding the polypeptides encoded by nacre polynucleotide sequences of the invention. These polynucleotide sequences are useful as probes, for example, for detecting nacre gene expression in a biological sample. They are also useful for producing nacrein and nacrein-related polypeptides or fragments thereof. The invention also provides nacrein and nacrein-related polypeptides which are useful, inter alia, for making antibodies or for detection of nacre gene expression in a biological sample and as a basis for rational polypeptide design. Further, the invention provides antibodies raised against nacrein and nacrein-related polypeptides or fragments thereof. The invention also provides methods using the nacre polynucleotides of the invention, such as methods of detecting nacre gene expression in a biological sample. The invention also provides methods of generating nacrein and nacrein-related polypeptides in vitro or in vivo. Other methods of the invention include screening methods for identifying pearl oysters capable of expressing nacrein. The invention also provides methods of identifying conditions suitable for pearl oyster cultivation, for example by assessing nacre gene expression under a culture condition of interest. The invention also provides compositions comprising polynucleotides and polypeptides (including antibodies) of the invention. These and other embodiments will be described in more detail below.

In another aspect, the invention provides arrays or microarrays comprising any of the polynucleotides, polypeptides and/or antibodies described herein. Methods using these arrays or microarrays, including any of the methods described herein, are also provided.

Definitions

As used herein, "nacre" or "nacre gene" refers to the pearl oyster gene known as such in the art and as described herein. As is understood in the art, the nacre gene includes not only the coding sequences, but may also include 5' and 3' flanking sequences. A "fragment" of a polynucleotide is a portion of a polynucleotide, and may contain coding and/or non-coding sequences. Preferably, a fragment of a polynucleotide comprises at least 10 contiguous nucleotides, more preferably at least 15, more preferably at least 25, more preferably at least 30, more preferably at least 50, more preferably at least 75, more preferably at least 100 contiguous nucleotides.

As used herein, a "nacre polynucleotide" refers to a polynucleotide of the present invention as described herein.

"Nacrein" refers to a protein (polypeptide) product encoded in the nacre gene. A nacrein-related polypeptide refers to polypeptides described herein (generally with sequences related to, i.e. homologous to, a sequence contained within the sequence depicted in SEQ ID NO:4), for example, to a polypeptide encoded by a polynucleotide comprising a sequence depicted in, for example, SEQ ID NO:1, wherein the sequence does not correspond identically in its entirety to any portion of the sequence shown in SEQ ID NOs:2 or 3 or any other known polynucleotide. In another example, nacrein-related polypeptide may refer to a polypeptide containing an amino acid sequence with at least 50%, more preferably at least 60%, even more preferably at least 70%, still more preferably at least 80%, and most preferably at least 90% sequence identity with a sequence in SEQ ID NO:4, wherein the sequence does not correspond identically in its entirety to any portion of the sequence shown in SEQ ID NOs:5 or 6 or any other known polypeptide. A nacrein-related polypeptide may or may not contain the entire sequence of a nacrein protein. A "fragment" of a polypeptide is a portion of a polypeptide. It is understood that a nacrein or nacrein-related polypeptide may exist in more than one form, such as a single nacrein or nacrein-related polypeptide, an assembly of at least one nacrein or nacrein-related polypeptide, and/or within a complex (i.e., comprising multi-subunits) containing at least one nacrein or nacrein-related polypeptide with at least one other polypeptide.

"Nacrein function" refers to an activity or characteristic associated with expression of nacre. The nature of these activity(s) or characteristic(s) depend upon the organism in which nacre function is found but generally appears to stem from transcriptional regulation (i.e. repression) of certain genes. These activities and characteristics include, but are not limited to, expression of nacre (i.e., transcription and translation of nacre), binding other proteins, regulation (whether induction or repression) of certain genes, and particular phenotypic characteristics.

As used herein, a "polynucleotide" is a polymeric form of nucleotides of any length, which contain deoxyribonucleotides, ribonucleotides, and/or their analogs. The terms "polynucleotide" and "nucleotide" as used herein are used interchangeably. Polynucleotides may have any three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double-stranded form and each of two complementary single-stranded forms known or predicted to make up the double stranded form. Not all linkages in a polynucleotide need be identical.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. The use of uracil as a substitute for thymine in a deoxyribonucleic acid is also considered an analogous form of pyrimidine.

If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications included in this definition are, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s).

Further, any of the hydroxyl groups ordinarily present in the sugars may be replaced by phosphonate groups, phosphate groups, protected by standard protecting groups, or activated to prepare additional linkages to additional nucleotides, or may be conjugated to solid supports. The 5' and 3' terminal OH groups can be phosphorylated or substituted with amines or organic capping group moieties of from 1 to 20 carbon atoms. Other hydroxyls may also be derivatized to standard protecting groups.

Polynucleotides can also contain analogous forms of ribose or deoxyribose sugars that are generally known in the art, including, but not limited to, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside.

Although conventional sugars and bases will be used in applying the method of the invention, substitution of analogous forms of sugars, purines and pyrimidines can be advantageous in designing a final product, as can alternative backbone structures like a polyamide backbone.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecule Biology* (F. M. Ausubel et al., eds., 1987) Supplement 30, section 7.718, Table 7.7.1. A preferred alignment program is ALIGN Plus (Scientific and Educational Software, Pennsylvania), preferably using default parameters, which are as follows: mismatch=2; open gap=0; extend gap=2. Another preferred alignment program is found in the NCBI Blast alignment program, preferably using its default parameters.

A polypeptide or polypeptide region has a certain percentage (for example, 80%, 85%, 90%, or 95%) of "sequence identity" to another sequence means that, when aligned, that percentage of amino acids are the same in comparing the two sequences. This alignment and the percent homology or sequence identity can be determined using homology search algorithms known in the art, for example the Smith-Waterman homology search algorithm (as taught in, for example, Smith and *Waterman, Adv. Appl. Math.* (1981), 2:482–489), preferably using an affine gap search with a gap open penalty of 12 and a gap extension penalty of 2, BLOSUM matrix of 62. Another preferred alignment program is found in the NCBI Blast alignment program, preferably using its default parameters.

A nucleotide is said to "encode" a polypeptide if, in its native state or when manipulated by methods well known to those skilled in the art, it can be transcribed and/or translated to produce the polypeptide or a fragment thereof. For purposes of this invention, and to avoid cumbersome referrals to complementary strands, the anti-sense (or complementary) strand of such a polynucleotide is also said to encode the sequence; that is, a polynucleotide sequence that "encodes" a polypeptide includes both the conventional coding strand and the complementary sequence (or strand).

A "primer" is a short polynucleotide, generally with a free 3'—OH group, that binds to a target potentially present in a sample of interest by hybridizing with the target, and thereafter promoting polymerization of a polynucleotide complementary to the target.

A "probe" when used in the context of polynucleotide manipulation refers to a polynucleotide which is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to, radioisotopes, fluorochromes, chemiluminescent compounds, dyes, and enzymes.

"Transformation" or "transfection" refers to the insertion of an exogenous polynucleotide into a host cell, irrespective of the method used for the insertion, for example, lipofection, transduction, infection or electroporation. The exogenous polynucleotide may be maintained as a non-integrated vector, for example, a plasmid, or alternatively, may be integrated into the host cell genome.

The terms "polypeptide", "oligopeptide", "peptide" and "protein" are used interchangeably herein to refer to polymers of amino acids of any length. The polymer may be linear or branched, it may comprise modified amino acids, it may be interrupted by non-amino acids, and it may be assembled into a complex of more than one polypeptide chain. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, where the polypeptides of this invention is an antibody, the polypeptides or fragment thereof can occur as single chains or associated chains.

A polypeptide "fragment" (also called a "region") of nacrein or nacrein-related polypeptide (or a "nacrein fragment" or "nacrein region") is a polypeptide comprising an amino acid sequence of nacrein or nacrein-related polypeptide that has at least 5 contiguous amino acids of a sequence of nacrein, more preferably at least 10 contiguous amino acids, more preferably at least about 15 contiguous amino acids, even more preferably at least about 25 contiguous amino acids, even more preferably at least about 30 contiguous amino acids, even more preferably at least about 40 contiguous amino acids, most preferably at least about 50 contiguous amino acids. A nacrein or nacrein-related polypeptide fragment may be characterized as having any of the following functions: (a) ability to bind another protein, particularly a protein associated with gene regulation; (b) ability to elicit a humoral and/or cellular immune response; (c) ability to regulate (i.e., repress or induce) another gene in the pathway regulated by nacrein; (d) ability to elicit a characteristic associated with nacrein function; (e) ability to elicit calcium carbonate aggregation; (e) ability to elicit pearl formation; (f) ability to inhibit pearl formation.

A "fusion polypeptide" is a polypeptide comprising regions in a different position than occurs in nature. The regions may normally exist in separate proteins and are brought together in the fusion polypeptide, or they may normally exist in the same protein but are placed in a new arrangement in the fusion polypeptide.

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions.

"Expression vectors" are defined as polynucleotides which, when introduced into an appropriate host cell, can be transcribed and translated into a polypeptide(s). An "expression system" usually connotes a suitable host cell comprised of an expression vector that can function to yield a desired expression product.

A "host cell" includes an individual cell or cell culture which can be or has been a recipient for vector(s) or for incorporation of nucleic acid molecules and/or proteins. Host cells include progeny of a single host cell, and the progeny may not necessarily be completely identical (in morphology or in genomic of total DNA complement) to the original parent cell due to natural, accidental, or deliberate mutation. A host cell includes cells transfected in vivo with a polynucleotide(s) of this invention.

As used herein, "expression" includes transcription and/or translation.

A "biological sample" encompasses a variety of sample types obtained from an individual. The definition encompasses tissue and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" also includes cells in culture, cell supernatants, cell lysates, biological fluid, and tissue samples.

"Heterologous" means derived from (i.e., obtained from) a genotypically distinct entity from the rest of the entity to which it is being compared. For example, a polynucleotide may be placed by genetic engineering techniques into a plasmid or vector derived from a different source, thus becoming a heterologous polynucleotide. A promoter which is linked to a coding sequence with which it is not naturally linked is a heterologous promoter.

An "isolated" or "purified" polynucleotide, polypeptide, antibody or cell is one that is substantially free of the materials with which it is associated in nature. By substantially free is meant at least 50%, preferably at least 70%, more preferably at least 80%, and even more preferably at least 90% free of the materials with which it is associated in nature. As used herein, an "isolated" polynucleotide or polypeptide also refers to recombinant polynucleotides or polypeptides, which, by virtue of origin or manipulation: (1) are not associated with all or a portion of a polynucleotide or polypeptide with which it is associated in nature, (2) are linked to a polynucleotide or polypeptide other than that to which it is linked in nature, or (3) does not occur in nature, or (4) in the case of polypeptides arise from expression of recombinant polynucleotides.

A "reagent" polynucleotide, polypeptide, or antibody, is a substance provided for a reaction, the substance having some known and desirable parameters for the reaction. A reaction mixture may also contain a "target", such as a polynucleotide, antibody, polypeptide, or assembly of polypeptides that the reagent is capable of reacting with.

A "stable duplex" of polynucleotides, or a "stable complex" formed between any two or more components in a biochemical reaction, refers to a duplex or complex that is sufficiently long-lasting to persist between formation of the duplex or complex and subsequent detection, including any optional washing steps or other manipulation that may take place in the interim.

As used herein, the term "agent" means a biological or chemical compound such as a simple or complex organic or inorganic molecule, a peptide, a protein, oligonucleotide, polynucleotide, carbohydrate, or lipoprotein. A vast array of compounds can be synthesized, for example oligomers, such as oligopeptides and oligonucleotides, and synthetic organic compounds based on various core structures, and these are also included in the term "agent". Compounds can be tested singly or in combination with one another.

An "individual" can be a vertebrate or invertebrate, which includes mollusks such pearl oyster (for example, *Pinctada margaritifera*).

An "antibody" (interchangeably used in plural form) is an immunoglobulin molecule capable of specific binding to a target, such as a polypeptide, through at least one antigen recognition site, located in the variable region of the immunoglobulin molecule. As used herein, the term encompasses not only intact antibodies, but also fragments thereof (such as Fab, Fab', F(ab')$_2$, Fv, single chain (ScFv), mutants thereof, fusion proteins, humanized antibodies, and any other modified configuration of the immunoglobulin molecule that comprises an antigen recognition site of the required specificity.

"Immunological recognition" or "immunological reactivity" refers to the specific binding of a target through at least one antigen recognition site in an immunoglobulin or a related molecule, such as a B cell receptor or a T cell receptor.

The term "antigen" refers to the target molecule that is specifically bound by an antibody through its antigen recognition site. The antigen may, but need not be chemically related to the immunogen that stimulated production of the antibody. The antigen may be polyvalent, or it may be a monovalent hapten. Examples of kinds of antigens that can be recognized by antibodies include polypeptides, polynucleotides, other antibody molecules, oligosaccharides, complex lipids, drugs, and chemicals.

An "immunogen" is an antigen capable of stimulating production of an antibody when injected into a suitable host, usually a mammal. Compounds may be rendered immunogenic by many techniques known in the art, including crosslinking or conjugating with a carrier to increase valency, mixing with a mitogen to increase the immune response, and combining with an adjuvant to enhance presentation.

"Microarray" and "array," as used interchangeably herein, comprise a surface with an array, preferably ordered array, of putative binding (e.g., by hybridization or polypeptide binding) sites for a biochemical sample (target) which often has undetermined characteristics. In a preferred embodiment, a microarray refers to an assembly of distinct polynucleotide or oligonucleotide probes or polypeptides (such as an antibody or antibody fragment) immobilized at defined positions on a substrate. Arrays are formed on substrates fabricated with materials such as paper, glass, plastic (e.g., polypropylene, nylon), polyacrylamide, nitrocellulose, silicon, optical fiber or any other suitable solid or semi-solid support, and configured in a planar (e.g., glass plates, silicon chips) or three-dimensional (e.g., pins, fibers, beads, particles, microtiter wells, capillaries) configuration. Probes forming the arrays may be attached to the substrate by any number of ways including (i) in situ synthesis (e.g., high-density oligonucleotide arrays) using photolithographic techniques (see, Fodor et al., *Science* (1991), 251:767–773; Pease et al., *Proc. Natl. Acad. Sci. U.S.A.* (1994), 91:5022–5026; Lockhart et al., *Nature Biotechnology* (1996), 14:1675; U.S. Pat. Nos. 5,578,832; 5,556,752; and 5,510,270); (ii) spotting/printing at medium to low-density (e.g., cDNA probes) on glass, nylon or nitrocellulose (Schena et al, *Science* (1995), 270:467–470, DeRisi et al,

*Nature Genetics* (1996), 14:457–460; Shalon et al., *Genome Res.* (1996), 6:639–645; and Schena et al., *Proc. Natl. Acad. Sci. U.S.A.* (1995), 93:10539–11286); (iii) by masking (Maskos and Southern, *Nuc. Acids. Res.* (1992), 20:1679–1684) and (iv) by dot-blotting on a nylon or nitrocellulose hybridization membrane (see, e.g., Sambrook et al., Eds., 1989, Molecular Cloning: A Laboratory Manual, 2nd ed., Vol. 1–3, Cold Spring Harbor Laboratory (Cold Spring Harbor, N.Y.)). Probes may also be noncovalently immobilized on the substrate by hybridization to anchors, by means of magnetic beads, or in a fluid phase such as in microtiter wells or capillaries. The probe molecules are generally nucleic acids such as DNA, RNA, PNA, and cDNA, proteins, polypeptides, oligosaccharides, cells, tissues and any permutations thereof which can specifically bind the target molecules.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as: "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991).

Polynucleotides of the Invention

The present invention provides nacre polynucleotides, in particular those comprising sequences from (related to) the nacre gene of *Pinctada margaritifera*, including polynucleotides with sequences of various percent identities in relation to the sequence of SEQ ID NO:1 as described herein. These polynucleotides include polynucleotides encoding polypeptide sequences of nacrein, in particular nacrein of *Pinctada margaritifera*. The invention further provides vectors containing these polynucleotides, host cells containing these polynucleotides, and compositions comprising these polynucleotides. These polynucleotides are isolated and/or produced by chemical and/or recombinant methods, or a combination of these methods. Unless specifically stated otherwise, the term "polynucleotides" shall include all embodiments of the polynucleotides of this invention.

The polynucleotides of this invention are useful as probes, primers, in expression systems, and in screening systems. Especially useful applications of the polynucleotides will be discussed below.

The cloning of a polynucleotide of the *Pinctada margaritifera* nacre gene is described in Example 1. A comparison between cDNA sequences from the nacre gene of *Pinctada margaritifera* (SEQ ID NO:1) and *Pinctada maxima* (SEQ ID NO:2) was performed using the NCBI BLAST program, using default parameters. This analysis indicated several regions of homology. The BLAST alignment indicated 89% identity between regions including nucleotides 1083–1869 of SEQ ID NO:1 and nucleotides 917–1706 of SEQ ID NO:2, 83% identity between regions including nucleotides 236–1328 of SEQ ID NO:1 and nucleotides 190–1247 of SEQ ID NO:2, 90% identity between regions including nucleotides 35–183 of SEQ ID NO:2 and nucleotides 1–183 of SEQ ID NO:2, 78% identity between regions including nucleotides 1224–1373 of SEQ ID NO:1 and nucleotides 851–994 of SEQ ID NO:2, 79% identity between regions including nucleotides 1337–1425 of SEQ ID NO:1 and nucleotides 748–836 of SEQ ID NO:2, 77% identity between regions including nucleotides 1254–1373 of SEQ ID NO:1 and nucleotides 731–853 of SEQ ID NO:2, 94% identity between regions including nucleotides 41–75 of SEQ ID NO:1 and 1721–1721 of SEQ ID NO:2, 75% identity between regions including nucleotides 1254–1430 of SEQ ID NO:1 and nucleotides 758–931 of SEQ ID NO:2, and 85% identity between regions including nucleotides 1338–1377 of SEQ ID NO:1 and nucleotides 731–770 of SEQ ID NO:2. A comparison between cDNA sequences from the nacre gene of *Pinctada margaritifera* (SEQ ID NO:1) and *Pinctada fucata* (SEQ ID NO:3) was also performed using the NCBI BLAST program, using default parameters. This analysis indicated several regions of homology. The BLAST alignment indicated 78% identity between regions including nucleotides 1515–1814 of SEQ ID NO:1 and nucleotides 1015–1314 of SEQ ID NO:3, 75% identity between regions including nucleotides 349–585 of SEQ ID NO:1 and nucleotides 311–563 of SEQ ID NO:3, 73% identity between regions including nucleotides 653–970 of SEQ ID NO:1 and nucleotides 618–956 of SEQ ID NO:3, 74% identity between regions including nucleotides 769–986 of SEQ ID NO:1 and nucleotides 767–990 of SEQ ID NO:3, 75% identity between regions including nucleotides 909–1106 of SEQ ID NO:1 and nucleotides 787–990 of SEQ ID NO:3, 81% identity between regions including nucleotides 255–319 of SEQ ID NO:1 and nucleotides 214–278 of SEQ ID NO:3, 73% identity between regions including nucleotides 960–1130 of SEQ ID NO:1 and nucleotides 748–927 of SEQ ID NO:3, and 81% identity between regions including nucleotides 1341–1388 of SEQ ID NO:1 and nucleotides 868–927 of SEQ ID NO:3.

In one embodiment, the invention provides polypeptides comprising the sequence depicted as amino acids 81–194 or 520–609 of SEQ ID NO:4. The invention further provides polypeptides comprising amino acid sequences with at least 50%, more preferably at least 60%, even more preferably at least 70%, still more preferably at least 80%, and most preferably at least 90% identity to the sequence of amino acids 81–194 or 520–609 of SEQ ID NO:4. The invention also provide fragments of the polypeptides, said fragments comprising at least 5, 10, 15, 20 or 30 contiguous nucleotides depicted in the sequence from amino acid 81–194 or 520–609 of SEQ ID NO:4. The invention also provide polynucleotides comprising a sequence encoding these polypeptides.

The invention includes modifications to the nacre polynucleotides described above such as deletions, substitutions, additions, or changes in the nature of any nucleic acid moieties. A "modification" is any difference in nucleotide sequence as compared to a polynucleotide shown herein to encode a nacrein or nacrein-related polypeptide, and/or any difference in terms of the nucleic acid moieties of the polynucleotide(s). Such changes can be useful to facilitate cloning and modifying expression of nacre polynucleotides. Such changes also can be useful for conferring desirable properties to the polynucleotide(s), such as stability. The definition of polynucleotide provided herein gives examples of these modifications. Hence, the invention also includes functionally-preserved variants of the nucleic acid sequences disclosed herein, which include nucleic acid substitutions, additions, and/or deletions.

The invention encompasses nacre polynucleotides including full-length (unprocessed), processed, coding, non-coding or portions thereof, provided that these polynucleotides contain a region encoding at least a portion of nacrein, in particular nacrein of *Pinctada margaritifera*. Also embodied are the mRNA and cDNA sequences and fragments thereof that include a portion encoding a nacrein or nacrein-related polypeptide segment as described herein.

The invention also encompasses polynucleotides encoding for functionally equivalent variants and derivatives of nacrein and nacrein-related polypeptides (in particular those derived from *Pinctada margaritifera*) and functionally equivalent fragments thereof which may enhance, decrease or not significantly affect properties of the polypeptides encoded thereby, provided that these functionally equivalent variants do not have the same amino acid sequence as depicted in SEQ ID NO:5 and 6. For instance, changes in a DNA sequence that do not change the encoded amino acid sequence, as well as those that result in conservative substitutions of amino acid residues, non-deleterious non-conservative substitutions, one or a few amino acid deletions or additions, and substitution of amino acid residues by amino acid analogs are those which will not significantly affect properties of the encoded polypeptide. Nucleotide substitutions that do not alter the amino acid residues encoded can be useful for optimizing gene expression in different systems. Suitable substitutions are known to those of skill in the art and are made, for instance, to reflect preferred codon usage in the particular expression systems. In another example, alternatively spliced polynucleotides can give rise to a functionally equivalent fragment or variant of *Pinctada margaritifera* nacrein or nacrein-related polypeptide. Alternatively processed polynucleotide sequence variants are defined as polynucleotide sequences corresponding to mRNAs that differ in sequence from one another but are derived from the same genomic region, for example, mRNAs that result from: 1) the use of alternative promoters; 2) the use of alternative polyadenylation sites; or 3) the use of alternative splice sites.

The nacre polynucleotides of the invention also include polynucleotides encoding fragments of nacrein or nacrein-related polypeptides, in particular those of *Pinctada margaritifera*. The polynucleotides encoding nacrein or nacrein-related polypeptide fragments are useful, for example, as probes, therapeutic agents, and as a template for encoding various functional and/or binding domains of nacrein, in particular nacrein of *Pinctada margaritifera*. Accordingly, the invention includes a polynucleotide that comprises a region of at least 10 contiguous nucleotides, preferably at least about 15 contiguous nucleotides, more preferably at least about 20 contiguous nucleotides, more preferably at least about 25 contiguous nucleotides, more preferably at least about 35 contiguous nucleotides, more preferably at least about 50 contiguous nucleotides, even more preferably at least about 75 contiguous nucleotides, even more preferably at least about 100 contiguous nucleotides, even more preferably at least about 200 contiguous nucleotides, even more preferably at least about 300 contiguous nucleotides.

In terms of hybridization conditions, the higher the sequence identity required, the more stringent are the hybridization conditions if such sequences are determined by their ability to hybridize to a sequence of SEQ ID NO:1. Accordingly, the invention also includes polynucleotides that are able to hybridize to a sequence comprising at least 20 contiguous nucleotides (or more, such as at least 25, 35, 40, 45, 50, 60, 75 or 100 contiguous nucleotides) of SEQ ID NO:1. The invention also provides polynucleotides that selectively hybridize to the sequence depicted in SEQ ID NO:1, relative to a known polynucleotide. The hybridization conditions can be stringent, for example, about 80° C. (or higher temperature) and 6M SSC (or less concentrated SSC), or moderately stringent, for example, about 60° C. (or higher, but less than about 80° C.) and 8M SSC (or less concentrated, but more concentrated than 6M). For discussion regarding hybridization reactions, see below.

Hybridization reactions can be performed under conditions of different "stringency". Conditions that increase stringency of a hybridization reaction are widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

"$T_m$" is the temperature in degrees Centigrade at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m = 81.5 + 16.6 \log [X^+] + 0.41(\% \ G/C) - 0.61(\% \ F) - 600/L$$

where [$X^+$] is the cation concentration (usually sodium ion, Na$^+$) in mol/L; (% G/C) is the number of G and C residues as a percentage of total residues in the duplex; (% F) is the percent formamide in solution (wt/vol); and L is the number of nucleotides in each strand of the duplex.

Compositions containing nacre polynucleotides are encompassed by this invention. The invention also provides compositions comprising a vector(s) containing a nacre polynucleotide as well as compositions comprising a host cell containing a nacre polynucleotide, as described herein. When these compositions are to be used pharmaceutically, they can be combined with a pharmaceutically acceptable excipient. Examples of pharmaceutically acceptable excipients are known in the art. When these compositions are to be used for detection, they are combined with a suitable substance such as a buffer, and they contain an amount effective to allow detection.

Preparation of Nacre Polynucleotides

The polynucleotides of this invention can be obtained using chemical synthesis, recombinant methods, or PCR.

Methods of chemical polynucleotide synthesis are well known in the art and need not be described in detail herein. One of skill in the art can use the sequences provided herein and a commercial DNA synthesizer to produce a desired DNA sequence.

For preparing nacre polynucleotides using recombinant methods, a polynucleotide comprising a desired sequence can be inserted into a suitable vector, and the vector in turn can be introduced into a suitable host cell for replication and amplification. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: *The Polymerase Chain Reaction*, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example.

Cloning and Expression Vectors Comprising a Nacre Polynucleotide

The present invention further includes a variety of vectors (i.e., cloning and expression vectors) having cloned therein nacre polynucleotide(s). These vectors can be used for expression of recombinant polypeptides as well as a source of nacre polynucleotides. Cloning vectors can be used to obtain replicate copies of the nacre polynucleotides they contain, or as a means of storing the polynucleotides in a depository for future recovery. Expression vectors (and host cells containing these expression vectors) can be used to obtain polypeptides produced from the polynucleotides they contain. They may also be used where it is desirable to express nacrein or nacrein-related polypeptides, in particular those of *Pinctada margaritifera*, in an individual, such as for eliciting pearl formation or for blocking pearl formation through inhibiting (such as by an antisense polynucleotide) a process(es) involved in pearl formation. Suitable cloning and expression vectors include any known in the art, e.g., those for use in bacterial, mammalian, yeast, insect and other expression systems. Specific vectors and suitable host cells are known in the art and need not be described in detail herein. For example, see Gacesa and Ramji, *Vectors*, John Wiley & Sons (1994).

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins substances, e.g., ampicillin, neomycin, methotrexate, etc.; (b) complement auxotrophic deficiencies; or (c) supply critical nutrients not available from complex media. The choice of the proper marker gene will depend on the host cell, and appropriate genes for different hosts are known in the art. Cloning and expression vectors also typically contain a replication system recognized by the host.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as Stratagem, and Invitrogen. The Examples provided herein also provide examples of cloning vectors.

Expression vectors generally are replicable polynucleotide constructs that contain a polynucleotide encoding a nacrein or nacrein-related polypeptide of interest. The polynucleotide encoding a nacrein or nacrein-related polypeptide is operatively linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) may be derived from nacre polynucleotides (i.e., the nacre gene of *Pinctada margaritifera*), or they may be heterologous (i.e., derived from other genes and/or other organisms). A polynucleotide sequence encoding a signal peptide can also be included to allow a nacrein or nacrein-related polypeptide to cross and/or lodge in cell membranes or be secreted from the call. A number of expression vectors suitable for expression in eukaryotic cells including yeast, avian, fish and mammalian cells are known in the art.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (where the vector is an infectious agent, such as vaccinia virus). The choice of means of introducing vectors or nacre polynucleotides will often depend on the host cell.

Host Cells Transformed with Polynucleotides of the Invention

Another embodiment of this invention are host cells transformed with (i.e., comprising) nacre polynucleotides and/or vectors having nacre polynucleotide(s) sequences, as described above. Both prokaryotic and eukaryotic host cells may be used. Prokaryotic hosts include bacterial cells, for example *E. coli, B. subtilis* and mycobacteria. *E. coli* cells are particularly useful for producing nacrein or nacrein-related polypeptides. See, for e.g., Komachi et al. (1994) *Genes Dev.* 8: 2857–2867. Among eukaryotic hosts are yeast, insect, avian, plant and mammalian cells. Host systems are known in the art and need not be described in detail herein. Examples of fungi (including yeast) host cells are *S. cerevisiae, Kluyveromyces lactis (K. lactis)*, species of *Candida* including *C. albicans* and *C. glabrata, C. maltosa, C. utilis, C. stellatoidea, C. parapsilosis, C. tropicalus, Neurospora crassa, Aspergillus nidulans, Schizosaccharomyces pombe (S. pombe), Pichia pastoris*, and *Yarowia lipolytica*.

The host cells of this invention can be used, inter alia, as repositories of nacre polynucleotides and/or vehicles for production of nacre polynucleotides and/or nacrein or nacrein-related polypeptides.

Uses for and Methods Using Polynucleotides of the Invention

The polynucleotides of this invention have several uses. Nacre polynucleotides are useful, for example, in expression systems for the recombinant production of nacre polynucleotides or fragments thereof. They are also useful as hybridization probes to assay for the presence of nacre polynucleotide (or related) sequences in a sample using methods well known to those in the art. Further, nacre polynucleotides are also useful as primers to effect amplification of desired polynucleotides. The nacre polynucleotides of this invention may also be useful as transgenes or antisense polynucleotides.

Nacre polynucleotides of this invention can be used as primers for amplification of polynucleotides encoding nacre polynucleotides and fragments thereof, such as in a polymerase chain reaction (PCR). PCR has been described above. The conditions for carrying out PCR reactions depend on the specificity desired, which in turn can be adjusted by the primer used and the reaction conditions. Such adjustments are known in the art and need not be discussed in detail herein.

The nacre polynucleotides of this invention can be used in expression systems to produce nacrein or nacrein-related polypeptides or recombinant forms of nacrein or nacrein-related polypeptides, which have enhanced, equivalent, or different, desirable properties. These recombinant forms are made by using routine methods in the art. Examples of recombinant forms of nacrein or nacrein-related polypeptides include, but are not limited to, fusion proteins. Fusion proteins may be used to regulate the expression of other genes in pearl oysters, such as *Pinctada margaritifera* and related oyster species. Fusion proteins may also facilitate purification.

Nacre polynucleotides may also be used in screening methods, as described herein. Further, nacre polynucleotides may be used to obtain other genes and gene products regulated by nacrein or otherwise involved in a nacrein pathway, as described herein.

Polypeptides of the Invention

The present invention encompasses nacrein and nacrein-related polypeptide sequences. The amino acid sequence of the longest open reading frame predicted from the nucleotide sequence depicted in SEQ ID NO:1 is represented in SEQ ID NO:4. The polypeptides of the invention may comprise any novel region (i.e., not disclosed in the public domain as of the filing date of this application) of SEQ ID NO: 4. The nacrein and nacrein-related polypeptides of this invention are identified and characterized by any of the following criteria: (a) ability to serve as an organic matrix for aggregation of calcium carbonate; (b) ability to facilitate pearl formation; (c) possess at least one of the characteristics that are desired in powdered pearl; and/or (d) ability to reduce pearl formation. Unless specifically stated, the term "polypeptide(s)" shall include all polypeptide embodiments of this invention.

The polypeptides have a variety of uses, including their use in making antibodies that bind to these polypeptides, their use as pharmaceuticals, their use in rational (i.e., structure-based) drug design, their use in isolating other gene(s) and gene product(s) that are regulated by nacrein, their use in cosmetical compositions (including for skin treatment and plastic surgery). The nacrein and nacrein-related polypeptides, in particular those comprising a polypeptide comprising the sequence, or portion thereof, depicted as amino acids 81–194 or 520–609 of SEQ ID NO:4 can be used as a basis for developing agents that affect the pearl formation process. As this sequence is highly homologous to carbonic anhydrase, polypeptides comprising sequences with a sufficient level of identity to the sequence from amino acid 81–194 or 520–609 of SEQ ID NO:4 can be developed as enhancers or blockers of carbonic anhydrase activity.

The predicted amino acid sequences for nacrein of *Pinctada margaritifera* (SEQ ID NO:4) and *Pinctada maxima* (SEQ ID NO:5) were compared with the NCBI BLAST program, using default parameters. This analysis indicated two regions of homology. The BLAST alignment indicated 54% identity between amino acids 20–197 of SEQ ID NO:4 and amino acids 15–233 of SEQ ID NO:5, and 79% identity between amino acids 490–609 of SEQ ID NO:4 and amino acids 328–445 of SEQ ID NO:5. The predicted amino acid sequences for nacrein of *Pinctada margaritifera* (SEQ ID NO:4) and *Pinctada fucata* (SEQ ID NO:6) were also compared with the NCBI BLAST program, using default parameters. As with the comparison with *Pinctada maxima*, above, the BLAST analysis indicated two regions of homology between the sequences of *Pinctada margaritifera* and *Pinctada fucata*. The BLAST alignment indicated 64% identity between amino acids 1–238 of SEQ ID NO:4 and 1–236 of SEQ ID NO:6, and 91% identity between amino acids 467–611 of SEQ ID NO:4 and amino acids 424–568 of SEQ ID NO:6.

The size of the nacrein or nacrein-related polypeptide fragments may vary widely, as the length required to effect activity could be as small as, for example, a 5-mer amino acid sequence to elicit an immune response, or a 30-mer to 40-mer amino acid sequence to effect binding to an antibody. The maximum length generally is not detrimental to effecting activity. The minimum size must be sufficient to provide a desired function. As is evident to one skilled in the art, these nacrein and nacrein-related polypeptides, regardless of their size, may also be associated with, or conjugated with, other substances or agents to facilitate, enhance, or modulate function and/or specificity of a nacrein or nacrein-related polypeptide.

The invention includes modifications to nacrein and nacrein-related polypeptides including functionally equivalent fragments of the nacrein polypeptides (for example, from another species, such as *Pinctada maxima* and/or *Pinctada fucata*) which do not significantly affect their properties and variants which have enhanced or decreased activity, provided that these sequences are different from those depicted in SEQ ID NOs:5 and 6. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified nacrein and nacrein-related polypeptides are made using established procedures in the art and can be screened using standard assays known in the art.

The invention also encompasses fusion proteins comprising one or more nacrein and/or nacrein-related polypeptides. For purposes of this invention, a nacrein fusion protein contains one or more nacrein and/or nacrein-related polypeptides and another amino acid sequence to which it is not attached in the native molecule, for example, a heterologous sequence or a homologous sequence from another region or from the nacrein protein of another species of pearl oyster (such as *Pinctada maxima* and *Pinctada fucata*). Useful heterologous sequences include, but are not limited to, sequences that provide for secretion from a host cell, or facilitate the coupling of the polypeptide to an immunoassay support. For instance, a useful heterologous sequence is one which facilitates purification. Examples of such sequences are known in the art and include those encoding epitopes such as Myc, HA (derived from influenza virus hemagglutinin), His-6, or FLAG. Other heterologous sequences that facilitate purification are derived from proteins such as glutathione S-transferase (GST), maltose-binding protein (MBP), or the Fc portion of immunoglobulin.

The invention also encompasses polymeric forms of nacrein and nacrein-related polypeptides. As used herein, a polymeric form of a nacrein or nacrein-related polypeptide contains a plurality (i.e., more than one) of nacrein and/or nacrein-related polypeptides. In one embodiment, linear polymers of nacrein and/or nacrein-related polypeptides are provided. These nacrein and/or nacrein-related linear polymers may be conjugated to carrier. These linear polymers can comprise multiple copies of a single nacrein or nacrein-related polypeptide, or combinations of different nacrein and/or nacrein-related polypeptides, and can have tandem nacrein and/or nacrein-related polypeptides, or nacrein and/or nacrein-related polypeptides separated by other amino acid sequences. These linear polymers can be made using standard recombinant methods well known in the art. In another embodiment, nacrein multiple antigen peptides (Maps) are provided. Maps have a small immunologically inert core having radically branching lysine dendrites, onto which a number of nacrein and/or nacrein-related polypeptides can be anchored (i.e., covalently attached). Posnett et al. (1988) *J. Biol. Chem.* 263:1719–1725; Tam (1989) *Meth. Enz.* 168:7–15. The result is a large macromolecule having a high molar ratio of nacrein and/or nacrein-related polypeptides to core. Maps are useful, efficient immunogens as well as useful antigens for assays such as ELISA. Nacrein or nacrein-related maps can be made synthetically and can be obtained commercially (Quality Controlled Biochemicals, Inc. Hopkinton, MA). In a typical MAP system, a core matrix is made up of three levels of lysine and eight amino acids for anchoring nacrein and/or nacrein-related polypeptides. The MAP may be synthesized by any method known in the art, for example. a solid-phase method, for example, R. B. Merrifield (1963) *J. Am. Chem. Soc.* 85:2149.

In another embodiment, nacrein and/or nacrein-related polypeptides can be conjugated with carrier or label. For example, in instances where the nacrein and/or nacrein-related polypeptide is correctly configured so as to provide a binding site, but is too small to be immunogenic, the polypeptide may be linked to a suitable carrier. A number of techniques for obtaining such linkage are known in the art. Any carrier can be used which does not itself induce the production of antibodies harmful to the host. Suitable carriers are typically large, slowly metabolized macromolecules such as proteins; polysaccharides, such as latex functionalized sepharose, agarose, cellulose, cellulose beads and the like; polymeric amino acids, such as polyglutamic acid, polylysine, and the like; amino acid copolymers; and inactive virus particles or attenuated bacteria, such as *Salmonella*. Especially useful protein substrates are serum albumins, keyhole limpet hemacyanin, immunoglobulin molecules, thyroglobulin, ovalbumin, tetanus toxoid, and other proteins well known to those of skill in the art. Labels are known in the art and are described herein.

Nacrein and nacrein-related polypeptides of the invention can be identified and/or characterized in a number of ways. For example, a nacrein and/or nacrein-related polypeptide can be tested for its ability to bind to, for instance, another protein (such as an antibody or a protein associated with gene regulation by interacting with full-length nacrein, in particular nacrein of *Pinctada margaritifera*), or an inorganic material such as calcium compounds, in particular calcium carbonate. A nacrein or nacrein-related polypeptide may also be tested for its ability to elicit or inhibit one or more characteristics associated with nacrein function, such as functions related to pearl formation. It is understood that only one of these properties need be present in order for a polypeptide to come within this invention, although more than one of these properties may be present. Screening such polypeptides is well within the skill of the art.

The ability of a nacrein and nacrein-related polypeptide to bind (i.e., interact with) another protein can be assessed using standard techniques in the art. Binding of a nacrein or nacrein-related polypeptide to an antibody may be assessed, for example, by RIA (i.e., by reacting radiolabelled nacrein or nacrein-related polypeptide with an antibody that is coated on microtiter plates). In another procedure, binding to an antibody is determined by competitive immunoassay. For example, a fragment is tested for its ability to interfere with the binding between the antibody and another polypeptide known to bind to the antibody. This assay may be conducted by labeling one of the components (i.e., antibody or polypeptide known to bind to the antibody), and optionally immobilizing the other member of the binding pair on a solid support for ease of separation. The test fragment is incubated with labeled region, and then the mixture is presented to the immobilized target to determine if the test fragment is able to inhibit binding.

In the case of testing whether the nacrein or nacrein-related polypeptide binds to another protein, for instance, a protein known to be involved in the pearl formation pathway, or a protein known to bind to nacrein, assays to detect binding are known in the art and need not be described in detail herein. For instance, a protein is immobilized on a suitable column. Extracts or solutions containing the test nacrein or nacrein-related polypeptide are then run through the column, and a determination is made whether the nacrein or nacrein-related polypeptide was retained on the column. Conversely, the nacrein or nacrein-related polypeptides can be immobilized on a column and cell extracts or lysates are allowed to run through the column.

For characterizing a nacrein or nacrein-related polypeptide for its ability to bind to an inorganic compound, such as calcium carbonate, formation of a complex of nacrein or nacrein-related and an inorganic compound can be assessed visually and/or using assays known in the art.

Compositions containing nacrein and/or nacrein polypeptides are encompassed by this invention. When these compositions are to be used pharmaceutically, they are combined with a pharmaceutically acceptable excipient. Examples of pharmaceutically acceptable excipients are known in the art.

When these compositions are to be used for detection, they are combined with a suitable substance such as a buffer, and they contain an amount effective to allow detection. When these compositions are to be used cosmetically, they are combined with a suitable cosmetic additive.

Preparation of Polypeptides of this Invention

The polypeptides of this invention can be made by procedures known in the art. The polypeptides can be produced by recombinant methods (i.e., single or fusion polypeptides) or by chemical synthesis. Polypeptides, especially shorter polypeptides up to about 50 amino acids, are conveniently made by chemical synthesis. Methods of chemical synthesis are known in the art and are commercially available. For example, a polypeptide could be produced by an automated polypeptide synthesizer employing the solid phase method. Polypeptides can also be made by chemical synthesis using techniques known in the art.

Polypeptides can also be made by expression systems, using recombinant methods. The availability of polynucleotides encoding polypeptides permits the construction of expression vectors encoding intact (i.e., native) polypeptide, functionally equivalent fragments thereof, or recombinant forms. A polynucleotide encoding the desired polypeptide, whether in fused or mature form, and whether or not containing a signal sequence to permit secretion, may be ligated into expression vectors suitable for any convenient host. Both eukaryotic and prokaryotic host systems can be used. The polypeptide is then isolated from lysed cells or from the culture medium and purified to the extent needed for its intended use. Purification or isolation of the polypeptides expressed in host systems can be accomplished by any method known in the art. For example, cDNA encoding a polypeptide intact or a fragment thereof can be operatively linked to a suitable promoter, inserted into an expression vector, and transfected into a suitable host cell. The host cell is then cultured under conditions that allow transcription and translation to occur, and the desired polypeptide is recovered. Other controlling transcription or translation segments, such as signal sequences that direct the polypeptide to a specific cell compartment (i.e., for secretion), can also be used. Examples of prokaryotic host cells are known in the art and include, for example, *E. coli* and *B. subtilis*. Examples of eukaryotic host cells are known in the art and include yeast, avian, insect, plant, and animal cells such as COS7, HeLa, CHO and other mammalian cells.

When using an expression system to produce nacrein or nacrein-related polypeptides, it is often preferable to construct a fusion protein that facilitates purification. Examples of components for these fusion proteins include, but are not limited to myc, HA, FLAG, His-6, glutathione S-transferease, maltose binding protein or the Fc portion of immunoglobulin. These methods are known in the art.

Preferably, especially if used for pharmaceutical, or cosmetic purposes, the polypeptides are at least partially purified or isolated from other cellular constituents. Preferably, the polypeptides are at least 50% pure. In this context, purity is calculated as a weight percent of the total protein content of the preparation. More preferably, the proteins are 50–75% pure. More highly purified polypeptides may also be obtained and are encompassed by the present invention. For surgical (clinical) use, the polypeptides are preferably highly purified, at least about 80% pure, and free of pyrogens and other contaminants. Methods of protein purification are known in the art.

Uses of Polypeptides

The polypeptides of this invention have a variety of uses. They may be used, for example, to raise antibodies in a suitable host, which may be rabbit, mouse, rat, goat, or human, as non-inclusive examples. It is possible that such antibodies, when administered to an organism expressing nacrein would modulate the amount of nacrein present in the individual, and thus modulate pearl formation. The polypeptides of this invention may be useful in pharmaceutical applications, such as in therapeutic and/or prophylactic compositions. The polypeptides may also be useful cosmetically. They may also be used clinically, such as in plastic surgery. Accordingly, the invention provides compositions comprising nacrein and nacrein-related polypeptides, said compositions capable of eliciting a desired effect in an individual when administered in an effective amount. In this context, an "effective amount" is an amount sufficient to elicit a desired effect response, and an effective amount may be administered in one or more administrations.

Nacrein and nacrein-related polypeptides may also be used an agent to screen pharmaceutical candidates (both in vitro and in vivo), for rational (i.e., structure-based) drug design, as well as possible therapeutic uses as described above. The nacrein and nacrein-related polypeptides may also be used to identify polypeptides, especially those from pearl oysters that bind (or interact physically) with nacrein and could thus themselves be drug targets.

Antibodies and their Preparation

Also provided by this invention are antibodies capable of specifically binding to nacrein and nacrein-related polypeptide(s) of this invention. The antibodies can be useful for, for example, screening purposes, as described more fully below. Antibodies of this invention can also be used for purification and/or isolation of polypeptides described herein.

In one embodiment, the invention provides a purified antibody capable of specifically binding to a polypeptide of this invention. As noted in the definition of "antibody" above, this includes fragments of antibodies, such as Fab fragments. In another embodiment, a monoclonal antibody is provided that is capable of specifically binding to a polypeptide of this invention.

Laboratory methods for producing polyclonal antibodies and monoclonal antibodies, as well as deducing their corresponding nucleic acid sequences, are known in the art. For example, see Harlow and Lane, *Antibodies: A Laboratory Manual*, Cold Spring Harbor Laboratory, New York (1988) and Sambrook et al. (1989).

The antibodies of this invention may be polyclonal or monoclonal. Monoclonal antibodies of this invention can be biologically produced by introducing a polypeptide (or fragment of a polypeptide) of this invention into an animal, e.g., mouse or rat. The antibody producing cells in the animal are isolated and fused with myeloma cells or heteromyeloma cells to produce hybrid cells or hybridomas. Accordingly, the invention also includes hybridoma cells producing the monoclonal antibodies of this invention.

Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski et al. (1985) *Proc. Natl. Acad. Sci.* 82:8653 or Spira et al. (1984) *J. Immunol. Methods* 74:307.

Thus, using the polypeptide(s) of this invention or fragment(s) thereof, and well known methods, one of skill in the art can produce and screen the hybridoma cells and antibodies of this invention for antibodies having the ability to bind polypeptide(s) of this invention.

If a monoclonal antibody being tested binds with a nacrein or nacrein-related polypeptide(s) of this invention, then the antibody being tested and the antibodies provided by the hybridomas of this invention are equivalent. It is also possible to determine without undue experimentation whether an antibody has the same specificity as a monoclonal antibody of this invention by determining whether the antibody being tested prevents a monoclonal antibody of this invention from binding the polypeptide(s) with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with the polypeptide(s) with which it is normally reactive, and determine if the monoclonal antibody being tested is inhibited in its ability to bind the antigen. If the monoclonal antibody being tested is inhibited, then, in all likelihood, it has the same, or a closely related, epitopic specificity as the monoclonal antibody of this invention.

As noted above, this invention also provides biological active fragments of the polyclonal and monoclonal antibodies described above. These antibody fragments retain some ability to selectively bind with its antigen or immunogen. Examples of antibody fragments are known in the art and include, but are not limited to, CDR regions, Fab, Fab', $F(ab')_2$, $F_v$, and single chain methods. Methods of making these fragments are known in the art, see for example, Harlow and Lane, (1988).

The antibodies of this invention also can be modified to create chimeric antibodies. Chimeric antibodies are those in which the various domains of the antibodies' heavy and light chains are coded for by DNA from more than one species.

The antibodies of this invention can be linked (i.e., conjugated) to a detectable agent or a hapten. The complex is useful to detect the polypeptide(s) (or polypeptide fragments) to which the antibody specifically binds in a sample, using standard immunochemical techniques such as immunohistochemistry as described by Harlow and Lane (1988). supra. Examples of types of immunoassays which can utilize monoclonal antibodies of the invention are competitive and non-competitive immunoassays in either a direct or indirect format. Examples of such immunoassays are the enzyme linked immunoassay (ELISA) radioimmunoassay (RIA) and the sandwich (immunometric) assay. Detection of using the monoclonal antibodies of the invention can be done by utilizing immunoassays which are run in either the forward, reverse, or simultaneous modes, including immunohistochemical assays on physiological samples. Those of skill in the art will know, or can readily discern, other immunoassay formats without undue experimentation.

Another technique which may also result in greater sensitivity consists of coupling the antibodies to low molecular weight haptens. These haptens can then be specifically detected by means of a second reaction. For example, it is common to use such haptens as biotin, which reacts avidin, or dinitropherryl, pyridoxal, and fluorescein, which can react with specific anti-hapten antibodies. See Harlow and Lane (1988) supra.

The monoclonal antibodies of the invention can be bound to many different carriers. Thus, this invention also provides compositions containing antibodies and a carrier. Carriers can be active and/or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, polypeptides of this invention may be detected by the monoclonal antibodies of the invention when present in biological samples, such as fluids and tissues.

Compositions containing the antibodies, fragments thereof or cell lines which produce the antibodies, are encompassed by this invention. When these compositions are to be used pharmaceutically, they are combined with a pharmaceutically acceptable excipient.

Methods Using Polynucleotides, Polypeptides and Antibodies of the Invention

The invention provides methods of using the nacre polynucleotides or antibodies to determine conditions suitable for pearl formation. Pearl formation requires the expression of nacre. Thus, detection of expression of the gene (for example, in the form of RNA transcripts or protein) would be indicative of pearl formation. Accordingly, methods of determining conditions that permit pearl formation (which may be indicated by, for example, aggregation of calcium carbonate) may comprise: (a) cultivating a pearl oyster under a particular condition of interest; and (b) detecting expression of nacre by contacting a sample from the oyster with a polynucleotide or antibody described herein.

The conditions to be determined can be any that are involved in cultivation of pearl oysters. Hence, these conditions would generally include conditions of the water in which pearl oysters are cultivated. These conditions may include water temperature, ionic strength (for example, salinity), depth, and presence of other organic and/or inorganic material (for example, nutrients required by the pearl oyster). These conditions may also include presence/absence of one or more agent(s) that enhance or inhibit the pearl formation process. Various methods of cultivating oysters are known in the art.

Gene expression can be detected by any of a variety of methods known in the art. Common methods include nucleic acid hybridization techniques such as in situ PCR, PCR amplification of nucleic acid in a sample, Northern blot hybridization, and in situ hybridization. Other common methods include detection of formation of antibody-antigen complexes. Antibody-antigen complexes can be detected by methods well known in the art.

Samples containing gene expression products can originate from any source suspected or known to contain the products. One site of nacre gene expression in pearl oysters such as *Pinctada margaritifera* is the mantle region of the oyster. Thus, a sample containing mantle tissue would be suitable for use in these methods.

The invention also provides methods for detecting and/or identifying a nacrein-expressing oyster. In pearl-producing oysters, identification of such oysters can be useful for selecting individual oysters as potential candidates for use as a pearl producing vessel. In oyster species not previously known to be capable of pearl formation, detection of nacre gene expression would indicate potential for use of oysters of that species in pearl formation. Methods of detecting a nacre gene-expressing oyster may comprise: (a) contacting a sample from an oyster of interest with a polynucleotide of the invention; and (b) detecting nacre gene expression based on hybridization of said polynucleotide to the sample. Methods of detecting a nacre-expressing oyster may also comprise: (a) contacting a sample from an oyster of interest with an antibody of the invention; and (b) detecting nacre gene expression based on binding of said antibody to the sample. Sample source and methods of detection are as described above.

Quantification of nacre gene expression in a sample can provide useful information in pearl oyster cultivation. As used herein, the term "cultivation" refers to care of pearl oysters under conditions that promote growth and pearl formation. Expression levels of nacre may be indicative of optimal cultivation conditions, individual oysters that are efficient in pearl formation, individual species that are particularly efficient in pearl formation, or presence/absence of one or more agents that enhance or inhibit the pearl formation process. The invention provides methods of quantifying nacre gene expression in a sample, said methods comprising (a) contacting the sample with a polynucleotide of the invention; (b) detecting hybridization of the polynucleotide to said sample; and (c) comparing the amount of the hybridization of step (b) with the amount of hybridization of said polynucleotide to a reference polynucleotide. A reference polynucleotide can be any polynucleotide whose amount is known and whose hybridization to the polynucleotide of step (b) provides a signal level that correlates to amount of nacre gene expression. Methods of quantification may also comprise: (a) contacting the sample with an antibody of the invention; (b) detecting binding of the antibody to said sample; and (c) comparing the amount of the binding of step (b) with the amount of binding of said antibody to a reference polypeptide. A reference polypeptide can be any polypeptide whose amount is known and whose binding to the antibody of step (b) provides a signal level that correlates to amount of nacre gene expression. Sample source and methods of detection are as described above.

Thus, as illustrated above, polynucleotides of the invention can be used as hybridization probes for detection of, for example, the presence of nacre polynucleotides in a cell. For instance, a nacre polynucleotide could be used as a probe to determine the presence of nacre polynucleotide sequences in oyster suspected but not known to be capable of pearl formation.

The polynucleotide probes may be provided with a label. Some of the labels often used include radioisotopes such as $^{32}P$ and $^{33}P$, chemiluminscent or fluorescent reagents such as fluorescein, and enzymes such as alkaline phosphatase that are capable of producing a colored solute or precipitant. The label may be intrinsic to the reagent, it may be attached by direct chemical linkage, or it may be connected through a series of intermediate reactive molecules, such as a biotin-avidin complex, or a series of inter-reactive polynucleotides. The label may be added to the reagent before hybridization with the target polynucleotide, or afterwards. To improve the sensitivity of the assay, it is often desirable to increase the signal ensuing from hybridization. This can be accomplished by using a combination of serially hybridizing polynucleotides or branched polynucleotides in such a way that multiple label components become incorporated into each complex. See U.S. Pat. No. 5,124,426.

If desired, the target polynucleotide may be extracted from the sample, and may also be partially purified. The target polynucleotide may be optionally subjected to any combination of additional treatments, including digestion with restriction endonucleases, size separation (by electrophoresis in agarose or polyacrylamide, for example), and affixation to a reaction matrix, such as a blotting material.

Hybridization is allowed to occur by mixing the nacre polynucleotide with a sample suspected of containing target polynucleotide under appropriate reaction conditions. This may be followed by washing or separation to remove unreacted reagent. Generally, both target polynucleotide and nacre polynucleotide are at least partly equilibrated into the single-stranded form (i.e., denatured) in order for complementary sequences to hybridize efficiently.

As stated above, another method of detecting polynucleotide target is by using PCR. All processes of producing replicate copies of the same polynucleotide, such as PCR or gene cloning, are collectively referred to herein as "replication". A polynucleotide of the invention (of suitable length, as can be determined by one skilled in the art) may be used to amplify nacre gene transcripts in the sample. Generally, a polynucleotide to be used as a primer is about 15 to 20 nucleotides in length, although longer primers of 30 to 50 nucleotides may be used. Preferably, a sample known not to contain any nacre gene sequences (in particular, *Pinctada margaritifera* nacre gene sequences) is used as a negative control. PCR methods are well known in the art and need not be described herein. For these methods, DNA or RNA is prepared from a sample.

Gene expression may be indicated by the presence of sufficient reaction product at the end of the amplification series. Amplified polynucleotide may be detected on an agarose gel upon staining with ethidium bromide. Alternatively, a radiolabeled substrate may be added to the mixture during the final amplification cycle. The incorporated label may be separated from unincorporated label (e.g., by blotting or by size separation) and the label may be detected by, for example, counting or autoradiography. If run on a gel of agarose or polyacrylamide, the size of the product may help confirm the identify of the amplified fragment. Specific amplification may also be followed by specific hybridization, by using the amplification mixture obtained from the foregoing procedure as a target source for the hybridization reaction outlined above.

As illustrated above, antibodies of the invention can be used as probes for detection of, for example, the presence of nacre gene product in a cell. For instance, an antibody could be used as a probe to determine the presence of nacrein in oyster suspected but not known to be capable of pearl formation.

The antibody used as a reagent may be provided directly with a suitable label. More frequently, the antibody is detected using one of a number of developing reagents which are easily produced or available commercially. Typically, these developing reagents are anti-immunoglobulin or protein A, and they typically bear labels which include, but are not limited to, fluorescent markers such as fluorescein, enzymes such as peroxidase that are capable of precipitating a suitable chemical compound, or that emits light by way of a chemical reaction, electron dense markers such as colloidal gold, or radioisotopes such as $^{125}$I, $^{32}$P, or $^{35}$S The amount of polypeptide may be detected in a standard quantitative immunoassay. If the protein is secreted or shed from the cell in any appreciable amount, or is present in white blood cells, it may be detectable in plasma or serum samples. Alternatively, the target protein may be solubilized or extracted from a solid tissue sample. Before quantitating, the protein may optionally be affixed to a solid phase, such as by a blot technique or using a capture antibody.

A number of immunoassay methods are established in the art for performing the quantitation. For example, the protein may be mixed with a pre-determined non-limiting amount of the reagent antibody specific for the protein. The reagent antibody may contain a directly attached label, such as an enzyme or a radioisotope, or a second labeled reagent may be added, such as anti-immunoglobulin or protein A. For a solid-phase assay, unreacted reagents are removed by washing. For a liquid-phase assay, unreacted reagents are removed by some other separation technique, such as filtration or chromatography. The amount of label captured in the complex is positively related to the amount of target protein present in the test sample. A variation of this technique is a competitive assay, in which the target protein competes with a labeled analog for binding sites on the specific antibody. In this case, the amount of label captured is negatively related to the amount of target protein present in a test sample. Results obtained using any such assay on a sample from a suspected infected source are compared with those from a non-infected source.

Polynucleotides of the invention can also be used to create transgenic organisms, such as transgenic oyster. Transgenesis methods are well known in the art. Transgenic organisms can be generated that possess a desired characteristic, for example increased pearl formation or formation of a pearl possessing a desired characteristic. In one embodiment, transgenic organisms comprising a polynucleotide comprising a sequence of *Pinctada margaritifera* (as depicted in SEQ ID NO:1) and one or more sequences of another oyster species (such as *Pinctada maxima* and *Pinctada fucata*, sequences as depicted in SEQ ID NO:2 and 3) can be generated. Such transgenic organisms can be selected for desired characteristics, for example increased pearl formation or formation of pearls with a desired characteristic. In some embodiments, a transgenic organism may be a non-human animal. Methods for generating transgenic animals via embryo manipulation and microinjection are known in the art and are described, for example, in U.S. Pat. Nos. 4,736,866, 4,870,009, 4,873,191, and in Hogan, B., *Manipulating the Mouse Embryo*, (Cold Spring Harbor Laboratory Press, Cold Spring Harbor, N.Y., 1986).

Arrays of Polynucleotides, Polypeptides and Antibodies of the Invention

The polynucleotides, polypeptides and/or antibodies of the invention can be attached to a solid or semi-solid substrate to create arrays. These arrays are useful in a variety of ways, including in carrying out the methods of the invention as described above.

Polynucleotides, polypeptides and/or antibodies of the invention can be attached to a solid or semi-solid support or surface, which may be made, e.g., from glass, plastic (e.g., polypropylene, nylon), polyacrylamide, nitrocellulose, or other materials.

Methods of attaching polynucleotides, polypeptides and proteins such as antibodies to solid or semi-solid substrates are well known in the art. For example, several techniques are known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into synthesized nucleic acids. The nucleic acid is then contacted with a solid substrate, such as a glass slide, which is coated with an aldehyde or another reactive group which will form a covalent link with the reactive group that is on the synthesized nucleic acid and become covalently attached to the glass slide. Microarrays comprising the polynucleotides can be fabricated using a Biodot (BioDot, Inc. Irvine, Calif.) spotting apparatus and aldehyde-coated glass slides (CEL Associates, Houston, Tex.). Polynucleotides can be spotted onto the aldehyde-coated slides, and processed according to published procedures (Schena et al., *Proc. Natl. Acad. Sci. U.S.A.* (1996), 93: 10614–10619). Arrays can also be printed by robotics onto glass, nylon (Ramsay, G., *Nature Biotechnol.* (1998), 16:40–44), polypropylene (Matson, et al., *Anal Biochem.* (1995), 224(1):110–6), and silicone slides (Marshall, A. and Hodgson, J., *Nature Biotechnol.* (1998), 16:27–31). Other approaches to array assembly include fine micropipetting within electric fields (Marshall and Hodgson, supra), and spotting the polynucleotides directly onto positively coated plates. Methods such as those using amino propyl silicon surface chemistry are also known in the art, as disclosed at http://www.cmt.corning.com and http://cmgm.stanford.edu/pbrown/.

One method for making microarrays is by making high-density arrays. For example, techniques are known for rapid deposition of polynucleotides (Blanchard et al., *Biosensors & Bioelectronics,* 11:687–690). Other methods for making microarrays, e.g., by masking (Maskos and Southern, *Nuc. Acids. Res.* (1992), 20:1679–1684), may also be used: In principle, and as noted above, any type of array, for example, dot blots on a nylon hybridization membrane, could be used. However, as will be recognized by those skilled in the art, very small arrays will frequently be preferred because hybridization volumes will be smaller.

Polynucleotides, polypeptides and/or antibodies of the invention may be spotted as a matrix on substrates comprising paper, glass, plastic, polypropylene, nylon, polyacrylamide, nitrocellulose, silicon, optical fiber or any other suitable solid or semi-solid (e.g., thin layer of polyacrylamide gel) (Khrapko, et al., *DNA Sequence* (1991), 1:375–388) surface.

An array may be assembled as a two-dimensional matrix on a planar substrate or may have a three-dimensional configuration comprising pins, rods, fibers, tapes, threads, beads, particles, microtiter wells, capillaries, cylinders and any other arrangement suitable for hybridization/binding and detection of target molecules. In one embodiment the substrate to which the polynucleotides, polypeptides and/or antibodies of the invention are attached is magnetic beads or particles. In another embodiment, the solid substrate comprises an optical fiber. In yet another embodiment, the polynucleotides, polypeptides and/or antibodies of the invention are dispersed in fluid phase within a capillary which, in turn, is immobilized with respect to a solid phase.

EXAMPLES

Example 1

Isolation of Sequences of the Nacre Gene of *Pinctada margaritifera*

Total RNA Isolation 9 grams of mantle tissue of *Pinctada margaritifera* was homogenized by using mortal and pestle in liquid nitrogen. The homogenized tissues was lysed in TRIZOL reagent (Life Technologies), followed by 12,000×g centrifugation for 20 minutes at 4° C. Total RNA in aqueous phase was then precipitated by adding isopropyl alcohol (½ of TRIZOL volume) and centrifuged at 8,000×g for 15 minutes at 4° C. The total RNA pellet was purified with 70% ethanol, followed by centrifugation, 8,000×g for 15 minutes at 4° C. The yield of total RNA was 3.2 mg as determined by spectrophotometric absorption measurements at 260 nm.

Isolation of Poly $A^+$ RNA from Total RNA

About 2 mg of total RNA was mixed with Oligotex suspension (QIAGEN), followed by 70° C. incubation for 3 minutes, which allowed mRNA to bind to $dT_{30}$ on Oligotex. The mRNA was eluted by resuspending in less ionic strength solutions and centrifugation. These procedures were repeated four times. The recovery yield of purified poly A+ mRNA was 20 ug.

cDNA Library Construction 15 ug of isolated and purified mRNA was used for making cDNA library by using the SuperScript Plasmid System (Life technologies). The first strand of DNA was synthesized by mixing purified mRNA with Not I primer-adapter, reverse transcriptase, followed by presence of *E. coli* DNA ligase and *E. coli* DNA polymerase I. The second strand synthesis was performed in the presence of T4 DNA polymerase, Sal I adapter and T4 DNA ligase. The synthesized cDNA then went through column chromatography for size fractionation, followed by ligation with pCMV-SPORT 6 vector.

Electroporation of cDNA Library into Competent Cells 1 ug of synthesized cDNA library was electroporated into XL1-Blue competent cells (Stratagene) by using the Gene Pulser II System (Bio-Rad). The procedure as described in Sambrook et al. (1989) was followed. Bacteria were then pasted onto LB plates with 25 ug/ml of ampicillin in the presence of X-gal (5-bromo-4-chloro-3-indolyl-b-D-galactopyranoside) and IPTG (Isopropyl-1-thio-b-D-galactopyranoside) for positive colony isolation, followed by incubation at 37° C. overnight.

RT-PCR

Purified mRNA was subjected to Reverse Transcriptase Polymerase Chain Reaction (RT-PCR) with deoxynucleotide triphosphates (dNTPs), reverse transcriptase, dithiothreitol (DTT), and random hexamer oligonucleotides. Conditions for PCR were hot start at 94° C. for 10 min; then 25 cycles of 94° C. for 1 min, 58° C. for 1 min, and 72° C. for 2 min; then 72° C. for 10 min. The RT-PCR product was then subcloned into the pGEM-T easy vector (Promega, Madison, Wis.) between EcoRI and SpeI, followed by electroporation as described above.

PCR Screening for Isolating Positive Clones

Clones obtained from the RT-PCR described above were randomly selected from LB plates for PCR screening by using T7 and Sp6 primers. Each bacterial clone was mixed with deoxynucleotide triphosphates (dNTPs), Taq polymerase, dithiothreitol, and subjected to 25 cycles of PCR, as described above, the amplification products assessed by 0.8% agarose gel electrophoresis.

Sequencing Screening for Verifying Positive Clones

Bacterial clones corresponding to PCR-gel electrophoresis with insert size larger than 300 bp were purified with mini-prep (VIOGENE) for DNA sequencing. Midi-prep and Mini-prep were based on a DNA alkaline extraction method. Plasmid DNA containing an insert was then sequenced by using the dideoxy terminator cycle sequencing method and DNA sequencer ABI 377 (Applied Biosystems). The primer used in DNA sequencing was either T7 or Sp6 primer.

Homology Analysis

DNA sequences obtained from previous step were searched against a gene database by using BLAST program (www.ncbi.nlm.nih.gov). Through BLAST searching, the sequence of one clone was determined to be that from the nacre gene cDNA.

Radioisotope-Labeled Probe

The obtained clone from homology analysis was then radioactively-labeled with $^{32}P$ by random priming, followed by spin column chromatography for isolation and purification of highly specific radioactively-labeled probes.

Hybridization with cDNA Library

Bacteria containing cDNA library DNA obtained from above were plated out on LB plate containing 25 ug/ml of ampicillin, followed by incubation at 37° C. for overnight. The plates were then attached with nylon membrane for replication, followed by DNA denaturing and hybridization with radioactively-labeled probes. The nylon membranes were then washed with low stringency SSC solution, followed by X-ray film photography. Positive clones were isolated from corresponding replicated plates for mini-prep and DNA sequencing verification.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated by the appended claims.

All publications, patents, and patent applications cited herein are hereby incorporated by reference in their entirety for all purposes to the same extent as if each individual publication, patent, or patent application were specifically and individually indicated to be so incorporated by reference.

We claim:

1. An isolated polynucleotide comprising: a) a polynucleotide having the coding sequence as shown in SEQ ID NO: 1, or its complement; or b) a fragment of said polynucleotide wherein said fragment is at least 100 nucleotides in length.

2. The polynucleotide of claim 1, wherein said polynucleotide consists of the sequence shown in SEQ ID NO: 1, or its complement, or a fragment thereof which is at least 100 nucleotides in length.

3. The polynucleotide according to claim 1, wherein said polynucleotide, or its complement or said fragment further comprises a detectable label.

4. The polynucleotide according to claim 1, wherein said polynucleotide, or its complement or said fragment is attached to a solid support.

5. A host cell comprising the isolated polynucleotide of claim 1.

6. An isolated polynucleotide encoding a polypeptide comprising the sequence depicted in SEQ ID NO:4.

7. The isolated polynucleotide of claim 6, wherein said polynucleotide is at least 3000 nucleotides.

8. An isolated polynucleotide according to claim 1, further comprising a sequence contained in SEQ ID NO:2.

9. The polynucleotide of claim 8, further comprising a sequence contained in SEQ ID NO:3.

10. An isolated polynucleotide according to claim 1, further comprising a sequence contained in SEQ ID NO:3.

11. An isolated polynucleotide comprising a sequence encoding nacrein of *Pinctada margaritifera*.

12. The isolated polynucleotide of claim 11, wherein said polynucleotide is between 1000 and 6000 nucleotides in length.

13. The isolated polynucleotide of claim 12, wherein said polynucleotide is between 1000 and 2000 nucleotides in length.

14. The isolated polynucleotide of claim 11, wherein said sequence is contained in SEQ ID NO:1.

15. A method of determining a condition that permits pearl formation, said method comprising:

a) cultivating a pearl oyster under a condition of interest; and b) detecting expression of nacre gene of the oyster by contacting a sample from the oyster with the polynucleotide of claim 1;

whereby detection of said expression indicates that said condition of interest permits pearl formation.

16. The method of claim 15, wherein said pearl oyster is of the species *Pinctada margaritifera*.

17. The method of claim 15, wherein said sample from the oyster comprises RNA.

18. The method of claim 17, wherein said sample is from mantle tissue.

19. A method of detecting a nacrein-expressing oyster, said method comprising:

(a) contacting a sample from said oyster with the polynucleotide of claim 1; and (b) detecting hybridization of said polynucleotide to the sample.

20. A method of quantifying nacre gene expression in a sample, said method comprising:

(a) contacting said sample with the polynucleotide of claim 1;

(b) detecting hybridization of said polynucleotide to said sample;

(c) comparing the amount of the hybridization of step (b) with the amount of hybridization of said polynucleotide to a reference polynucleotide.

21. The method of claim 20, wherein said sample is obtained from a pearl oyster.

22. An isolated polynucleotide according to claim 6, comprising a sequence encoding amino acids 81–194 of SEQ ID NO:4.

23. An isolated polynucleotide according to claim 6, comprising a sequence encoding amino acids 520–609 of SEQ ID NO:4.

24. An isolated polynucleotide according to claim 6, comprising a sequence encoding amino acids 81–194 and 520–609 of SEQ ID NO:4.

* * * * *

SEQUENCE LISTING

<160> NUMBER OF SEQ ID NOS: 6

<210> SEQ ID NO 1
<211> LENGTH: 2050
<212> TYPE: DNA
<213> ORGANISM: Pinctada margaritifera

<400> SEQUENCE: 1

```
ggcatttcaa aacttacaag agagagatac agtaaatgtg gagaatgacg acacttcttc      60
acttgactcc tctgcttgtt ctgattccat tatgtcattg tgcctccatg cacaggcatg     120
accattatat ggacatggat aaaacctacc gtaatcgatg gggaaactgt cattattcag     180
ggggaagtag ctgtgacgcc gggtttagct acaataggga acaaaatgag gaacaatgcc     240
acggtccgta tgactggcac actatatcta gttgctttaa ggcatgtgga agtaaagaga     300
gacaatcacc aatcaacatt tggtcacata gagccctttt ccgaaaactg ccaagactga     360
aattcaagcc acatatgaaa tcattggata cgaaagtgtc aaatcaccaa atcatgccc      420
ctgaattcga ttcagaggac gaaaaacttc atgttaaact gaagaatctt gttgatggac     480
attataaatt ccgcaatctc catattcaca ttggcaaaag tagacgaaag ggctccgaac     540
acagcgttga cagacatttt acacctatgg aggctcattt agtgttccgt catgatgaga     600
aaaggaaat caaacctcct aggatttggt taggaagaaa tttcagtgga attaatgaat      660
ttgttgtcgt tggggttttt ctagaggttg gtgatgaagg atacggtgat gaaccggacg     720
acgatgaatg taagcgcata ttaaagggtc attacgatca ttgcgacaac aatggagaca     780
acggctacaa ctgtgataac ggcaacaatg gaaacaacgg aaacaatggt aatggtaaca     840
acggttataa cggtaacaac ggttataacg gtaataacgg tgacaatggc aacagtggaa     900
acaatggtaa tggtaacaac ggttataacg gtaacaacgg ttataacggt aataacggtg     960
acaatggcaa cagcggaaac aatggtaatg gtaacaacgg ttataacggt aataacggtg    1020
gcaacggaaa caacagaaac aatggcaatg gtaacaacgg ttataacggt aataacggtg    1080
acaatggcaa caacggaaac aatggtaatg gtaacaacgg aaacaatggt aatgataaca    1140
acggaaataa tggtaatggt aacaacggaa ataacggtgg caatggcaac aatggaaaca    1200
atggtaatgg taacaacgga ataatggta atggtaacaa cggaaataat ggtaatggta    1260
acaacggaaa taacggtggc aatggcaaca atgtaatgg taacaatgga aataatggta    1320
acggtgacta cggtagtaat ggtaacaatg gtggaaacgg gaacaatggt aatacggtg    1380
ataacggtaa tggcgacaat ggttataacg gtgataatgg taacagtgac gggcgactca    1440
gacgttggga cttggaaaat gtccgacgca tgcataccga gcgatatcac ttcagcagaa    1500
gatgtattgt caaaaaagca aaacgcctca gcaggattct cgaatgcgca tatagacaca    1560
aaaaagtcag agaattcaaa aggaatggag aacacaaagg tcttgatgtt gaaattacac    1620
cggaaatggt tttaccgcca ataaagtaca gacaatacta tacctatgaa ggatcattga    1680
caaccctcc ttgcgatgag accgtccttt gggttgtaga aaaatgccac gtgcaagtat     1740
ccagaagggt gcttgatgca ttgcggaacg ttgaaggata tgaggatggt accacgctga    1800
gcaagtatgg aactagacgt cccacacaga gaaacataaa acctttaact gtgtacaaaa    1860
acttcatatg atcgaactca ttttctgttc cagtctcgtt aaggaacaaa tgtaaataat    1920
gtcacgattc gcacaatgta caatatatct gtttctgcac atcatatgaa gcatactcta    1980
atgtaaaact gttaaaaatg atgcaataaa tatgtttttt taaaaaaaaa aaaaaaaaa     2040
```

|  | 2050 |
|---|---|
| aaaaaaaaaa |  |

<210> SEQ ID NO 2
<211> LENGTH: 1811
<212> TYPE: DNA
<213> ORGANISM: Pinctada maxima

<400> SEQUENCE: 2

| | |
|---|---:|
| aatgtggaga atgacgacgc ttcttcactt gactgctctg cttgttctga ttccattatg | 60 |
| tcattgcgcc tccatgcaca ggcatgacca ttatatggac atggatcaaa cctaccctaa | 120 |
| tggattggga tactgtgaac cttcaggtga aagcagctgt aaagccggat ttagctacaa | 180 |
| tagagacata tgccaaggtc cgtatcattg cacactata tctagttgct ataaggcatg | 240 |
| tggacataaa aggagacaat caccaatcaa catttggtca cataaagctg tattcttacc | 300 |
| ttatctgcca agactgaaat tcaagccaca tatgaagtca ttggatacgg acgtgacaaa | 360 |
| tcaccaaaat cgtgcccctg aattcgagcc ggaggacgga gataagcttc atgtgaaact | 420 |
| aaagaatctt gttgatggac attataaatt tcacaatctc catattcaca acggcaaaag | 480 |
| tagacgaaag ggctcggaac acagcgtgaa cagacatttt acgcccatgg aggctcattt | 540 |
| ggtgttccat catgatgata aaaggaaat caaacctcca agggttaagt taggggagt | 600 |
| gtacgctggt cgtaacaaat ttgttgtcgt tggagtcttt ctagaggtgg gtgatgaagg | 660 |
| atacggtgat gaaccggacg acgatgaatg taagcgcata ttaaagggtc attgcgagaa | 720 |
| caatggggac aatggtaaca actgtgataa cggcaacaat ggtaacaacg acaacaatgg | 780 |
| taacaacgga acaatggta atggtaacaa cggttataac ggtaataacg gtgacaatgg | 840 |
| aaacaatggc aatggtaatg gtaacaacgg ttataacggt aataacggtt acaatggcaa | 900 |
| caacggaaac aatggtaatg gtaacaatga caataatggt aacgataaca acggaaataa | 960 |
| cggtggcaat ggtaacaacg gaaacaatgg taatggtaac aatggaaata atggtaatgg | 1020 |
| taataacgga aataacggtg gcaatggcaa caacggaaac aatggtaata gtaacaacgg | 1080 |
| aaataatggt aatggtaaca acggaaataa cggtggcaat ggcaacaacg gaaacaatgg | 1140 |
| taatggtaac aatgaaaata atggtaacgg tagtaatggt aacaatggtg gaaacggcaa | 1200 |
| caatggtaat aacggtgata acggtaatgg cgacaatggt tataacgtg ataatggtaa | 1260 |
| cagtgacggg cgactcagac gctgggattt ggcaaatgtc cgacgcatgc acgccgagcg | 1320 |
| atatcacttt agcggaggat gtatcgtcaa aaaagctaaa cgcctcagca ggattcttga | 1380 |
| atgcgcatat agacacaaaa aagtcagaga attcaaaagg aatggagaag aaaaaggtct | 1440 |
| tgatgttgat attacaccgg aaatggtttt accgccaatg aaatacagac attactatac | 1500 |
| ttatgaagga tctttgacaa cccctccttg caatgagacc gtcctttggg ttgttgaaaa | 1560 |
| atgccacgtg caagtatcca gaagggtgct tgatgcattg cggaacgtcg aaggatatga | 1620 |
| agatggtacc acgctgagca agtatggaac cagacgtccc acacaaagaa acaagcatcc | 1680 |
| tctacgtgtg tacaaaaact ccatataatg atcatggcga gagaatgacg acgcttcttc | 1740 |
| acttgactgc tctgcctcct cccccaccc ccccggcc atatggccac tctgcgttga | 1800 |
| taccactgct t | 1811 |

<210> SEQ ID NO 3
<211> LENGTH: 2363
<212> TYPE: DNA
<213> ORGANISM: Pinctada fucata -continued

```
<400> SEQUENCE: 3
tagtaaatgt gaagattggt gatgtatctt catttgactg ccctatgtgt tgttattccg      60
ctgtgttatg cgcctccat gttaaacat gaccactaca tggacaatgg tgtgaggtat      120
cctaatggtg acggaatctg taaacaattg aatgaaacca aatgtgatgc agggtttagc      180
tatgatagga gtatatgtga aggtcctcat tattggcaca ccatatcgaa atgcttcatt      240
gcatgtggaa ttggacagag acaatctcca atcaacatcg tttcttatga tgctaaattt      300
cgtcagcgtt tgccaaaatt gaaattcaag ccacatatgg agaaattaaa aacagaagtg      360
accaatcatc agaaccgagc tccagagttc gagccagagg atggggaaaa tctgtacgtg      420 aagctaaaata acctagtgga cggtcattat aaattccata atcttcacgt tcataatggt      480
agaaccagac gtaagggatc agaacacagt gttaacggtc gtttcacacc tatggaggct      540
catttggttt tccatcatga tgatcaaaca cactttgaac ctacacgcac taagctggga      600
ggagcattcc ctggtcataa cgattttgtc gtcgttggga ttttcttga ggtcggagat      660 gacggctttg gcgacgaacc ggatgacgaa gaatgtaaac acatcttaaa gggacatcac      720
cctgataata acgagaacgg caatggagac aatggcaata acggctacaa tggggacaac      780
ggtaacaatg gtgacaacgg caataacagc tacaatgggg acaacggtaa caatggtgtc      840
aacggcaata acggctacaa tggggacaac ggtaacaatg gagacaacgg caataacggc      900 tacaatggg acaacggtaa caatggtgac aacggcaata acggtgaaaa cggcaataac      960
ggtgaaaacg gcaataacgg tgaaaatggt cacaaacacg gatgtcgggt aaagaaagca     1020
aagcatctca gtaggatcct ggaatgtgct tatagaaacg ataaggtcag agagttcaag     1080
aaagttggag aagaggaagg gttagatgtt catctaacac cggagatggc tttgccgcca     1140
ctgaagtaca gacattacta tacatacgag ggatccctga ccactccccc gtgtacagag     1200
tctgtcctct gggttgttca aaaatgccat gtgcaggtgt caagaagggt tcttcatgca     1260
ttacgaaatg ttgaaggata taaagatggt accacactaa gaaagtatgg aactagacgt     1320
ccaacgcaaa agaataaagt tactgtgtac aaaagcttca aatagttgac atagtttttg     1380 ttctttcct tatagagaca tgtaacacag ccaattatgt ttcatatgta atccatgtaa     1440
aatacaggat ctttacataa atattcatgt gaaacaagca cgaacattaa aggactaggt     1500
gcgctaaccc cttatatcgg ccctataatt tcgacgagaa atgctttaa taaacaaact     1560 attaattata gcttttgca atgttgaatg tttgagaaaa taccgcatca tattttttag     1620
ccctcgtaac gtcacgcgag tgatgtatga tgtcatgttc tgaaagtcat ttgccctgaa     1680
tgacgcaaaa caaatgagaa tcatcgtatt ttacatacaa atcttcaaat tcatctgcga     1740
ttcaggcctc gaacacgata tttttatgc aaatttaaag gccgatcaaa aatccatcga     1800
ttagtacaaa tattatcgtg ggcaattaag gcctggaacg atacttaatt tcataaattt     1860
taatcgaaat ttcgctgatt tattgatatt ttcaatgagt ttcaacgttt tagacatttt     1920
tttgtaatat tcagtatagg actatgaaat caaaaaaagc tttcctgata tggattcacc     1980
atacatttaa catttcaaaa actagaatat tatggatata tgaacaactt tgaaaatggg     2040
gccgatatgg caggttaccg aacctacttc tttttatcaa attttttaca tgaaattcat     2100
gggaagtttc cgacatcaat ttcatgtgaa ttctatatcg catgaaggtc acaaagaaaa     2160
tttcatgtaa aattcatgcg aaggaaattc atgtgaaact catgtgaaat attttttcaca     2220 taaatcttaa gtgaaagta tataaatttc acaactttca tgtgaaattt aagtgatgct     2280
cattttgtat ggatttcatg tgaggcataa ttgactgctt gtactatgta attagaacaa     2340
```

-continued aatgtcaaat atttaataaa tga                                               2363

<210> SEQ ID NO 4
<211> LENGTH: 611
<212> TYPE: PRT
<213> ORGANISM: Pinctada margaritifera

<400> SEQUENCE: 4

Met Trp Arg Met Thr Thr Leu Leu His Leu Thr Pro Leu Leu Val Leu
 1               5                  10                  15

Ile Pro Leu Cys His Cys Ala Ser Met His Arg His Asp His Tyr Met
            20                  25                  30

Asp Met Asp Lys Thr Tyr Arg Asn Arg Trp Gly Asn Cys His Tyr Ser
        35                  40                  45

Gly Gly Ser Ser Cys Asp Ala Gly Phe Ser Tyr Asn Arg Glu Gln Asn
    50                  55                  60

Glu Glu Gln Cys His Gly Pro Tyr Asp Trp His Thr Ile Ser Ser Cys
65                  70                  75                  80

Phe Lys Ala Cys Gly Ser Lys Glu Arg Gln Ser Pro Ile Asn Ile Trp
                85                  90                  95

Ser His Arg Ala Leu Phe Arg Lys Leu Pro Arg Leu Lys Phe Lys Pro
            100                 105                 110

His Met Lys Ser Leu Asp Thr Lys Val Ser Asn His Gln Asn His Ala
        115                 120                 125

Pro Glu Phe Asp Ser Glu Asp Glu Lys Leu His Val Lys Leu Lys Asn
    130                 135                 140

Leu Val Asp Gly His Tyr Lys Phe Arg Asn Leu His Ile His Ile Gly
145                 150                 155                 160

Lys Ser Arg Arg Lys Gly Ser Glu His Ser Val Asp Arg His Phe Thr
                165                 170                 175

Pro Met Glu Ala His Leu Val Phe Arg His Asp Glu Lys Lys Glu Ile
            180                 185                 190

Lys Pro Pro Arg Ile Trp Leu Gly Arg Asn Phe Ser Gly Ile Asn Glu
        195                 200                 205

Phe Val Val Gly Val Phe Leu Glu Val Gly Asp Glu Gly Tyr Gly
    210                 215                 220

Asp Glu Pro Asp Asp Glu Cys Lys Arg Ile Leu Lys Gly His Tyr
225                 230                 235                 240

Asp His Cys Asp Asn Gly Asp Asn Gly Tyr Asn Cys Asp Asn Gly
                245                 250                 255

Asn Asn Gly Asn Asn Gly Asn Asn Gly Asn Gly Asn Asn Gly Tyr Asn
            260                 265                 270

Gly Asn Asn Gly Tyr Asn Gly Asn Asn Gly Asp Asn Gly Asn Ser Gly
        275                 280                 285

Asn Asn Gly Asn Gly Asn Asn Gly Tyr Asn Gly Asn Asn Gly Tyr Asn
    290                 295                 300

Gly Asn Asn Gly Asp Asn Gly Asn Ser Gly Asn Asn Gly Asn Gly Asn
305                 310                 315                 320

Asn Gly Tyr Asn Gly Asn Asn Gly Gly Asn Gly Asn Asn Arg Asn Asn
                325                 330                 335

Gly Asn Gly Asn Asn Gly Tyr Asn Gly Asn Asn Gly Asp Asn Gly Asn
            340                 345                 350

Asn Gly Asn Asn Gly Asn Gly Asn Asn Gly Asn Asn Gly Asn Asp Asn
        355                 360                 365

```
Asn Gly Asn Asn Gly Asn Gly Asn Asn Gly Asn Asn Gly Asn Gly
        370                 375                 380
Asn Asn Gly Asn Gly Asn Gly Asn Gly Asn Asn Gly Asn Asn Gly
385                 390                 395                 400
Asn Asn Gly Asn Asn Gly Asn Gly Asn Asn Gly Asn Gly Gly Asn
                405                 410                 415
Gly Asn Asn Gly Asn Gly Asn Asn Gly Asn Asn Gly Asn Asp Tyr
                    420                 425                 430
Gly Ser Asn Gly Asn Asn Gly Gly Asn Gly Asn Asn Gly Asn Asn Gly
            435                 440                 445
Asp Asn Gly Asn Gly Asp Asn Gly Tyr Asn Gly Asp Asn Gly Asn Ser
        450                 455                 460
Asp Gly Arg Leu Arg Arg Trp Asp Leu Glu Asn Val Arg Arg Met His
465                 470                 475                 480
Thr Glu Arg Tyr His Phe Ser Arg Arg Cys Ile Val Lys Lys Ala Lys
                    485                 490                 495
Arg Leu Ser Arg Ile Leu Glu Cys Ala Tyr Arg His Lys Lys Val Arg
                500                 505                 510
Glu Phe Lys Arg Asn Gly Glu His Lys Gly Leu Asp Val Glu Ile Thr
            515                 520                 525
Pro Glu Met Val Leu Pro Pro Ile Lys Tyr Arg Gln Tyr Tyr Thr Tyr
        530                 535                 540
Glu Gly Ser Leu Thr Thr Pro Pro Cys Asp Glu Thr Val Leu Trp Val
545                 550                 555                 560
Val Glu Lys Cys His Val Gln Val Ser Arg Arg Val Leu Asp Ala Leu
                    565                 570                 575
Arg Asn Val Glu Gly Tyr Glu Asp Gly Thr Thr Leu Ser Lys Tyr Gly
                580                 585                 590
Thr Arg Arg Pro Thr Gln Arg Asn Ile Lys Pro Leu Thr Val Tyr Lys
            595                 600                 605
Asn Phe Ile
    610

<210> SEQ ID NO 5
<211> LENGTH: 568
<212> TYPE: PRT
<213> ORGANISM: Pinctada maxima

<400> SEQUENCE: 5

Met Trp Arg Met Thr Thr Leu Leu His Leu Thr Ala Leu Leu Val Leu
1               5                   10                  15
Ile Pro Leu Cys His Cys Ala Ser Met His Arg His Asp His Tyr Met
                20                  25                  30
Asp Met Asp Gln Thr Tyr Pro Asn Gly Leu Gly Tyr Cys Glu Pro Ser
            35                  40                  45
Gly Glu Ser Ser Cys Lys Ala Gly Phe Ser Tyr Asn Arg Asp Ile Cys
        50                  55                  60
Gln Gly Pro Tyr His Trp His Thr Ile Ser Ser Cys Tyr Lys Ala Cys
65                  70                  75                  80
Gly His Lys Arg Arg Gln Ser Pro Ile Asn Ile Trp Ser His Lys Ala
                    85                  90                  95
Val Phe Leu Pro Tyr Leu Pro Arg Leu Lys Phe Lys Pro His Met Lys
                100                 105                 110
Ser Leu Asp Thr Asp Val Thr Asn His Gln Asn Arg Ala Pro Glu Phe
```

-continued

```
            115                 120                 125
Glu Pro Glu Asp Gly Asp Lys Leu His Val Lys Leu Lys Asn Leu Val
    130                 135                 140

Asp Gly His Tyr Lys Phe His Asn Leu His Ile His Asn Gly Lys Ser
145                 150                 155                 160

Arg Arg Lys Gly Ser Glu His Ser Val Asn Arg His Phe Thr Pro Met
                165                 170                 175

Glu Ala His Leu Val Phe His His Asp Asp Lys Lys Glu Ile Lys Pro
            180                 185                 190

Pro Arg Val Lys Leu Gly Gly Val Tyr Ala Gly Arg Asn Lys Phe Val
        195                 200                 205

Val Val Gly Val Phe Leu Glu Val Gly Asp Glu Gly Tyr Gly Asp Glu
    210                 215                 220

Pro Asp Asp Asp Glu Cys Lys Arg Ile Leu Lys Gly His Cys Glu Asn
225                 230                 235                 240

Asn Gly Asp Asn Gly Asn Asn Cys Asp Asn Gly Asn Asn Gly Asn Asn
                245                 250                 255

Asp Asn Asn Gly Asn Asn Gly Asn Asn Gly Asn Gly Asn Asn Gly Tyr
            260                 265                 270

Asn Gly Asn Asn Gly Asp Asn Gly Asn Asn Gly Asn Gly Asn Gly Asn
        275                 280                 285

Asn Gly Tyr Asn Gly Asn Asn Gly Tyr Asn Gly Asn Asn Gly Asn Asn
    290                 295                 300

Gly Asn Gly Asn Asn Asp Asn Asn Gly Asn Asp Asn Gly Asn Asn
305                 310                 315                 320

Gly Gly Asn Gly Asn Asn Gly Asn Asn Gly Asn Gly Asn Asn Gly Asn
                325                 330                 335

Asn Gly Asn Gly Asn Asn Gly Asn Asn Gly Gly Asn Gly Asn Asn Gly
            340                 345                 350

Asn Asn Gly Asn Ser Asn Asn Gly Asn Asn Gly Asn Gly Asn Asn Gly
        355                 360                 365

Asn Asn Gly Gly Asn Gly Asn Asn Gly Asn Asn Gly Asn Gly Asn Asn
    370                 375                 380

Glu Asn Asn Gly Asn Gly Ser Asn Gly Asn Asn Gly Gly Asn Gly Asn
385                 390                 395                 400

Asn Gly Asn Asn Gly Asp Asn Gly Asn Gly Asp Asn Gly Tyr Asn Gly
                405                 410                 415

Asp Asn Gly Asn Ser Asp Gly Arg Leu Arg Arg Trp Asp Leu Ala Asn
            420                 425                 430

Val Arg Arg Met His Ala Glu Arg Tyr His Phe Ser Gly Gly Cys Ile
        435                 440                 445

Val Lys Lys Ala Lys Arg Leu Ser Arg Ile Leu Glu Cys Ala Tyr Arg
    450                 455                 460

His Lys Lys Val Arg Glu Phe Lys Arg Asn Gly Glu Glu Lys Gly Leu
465                 470                 475                 480

Asp Val Asp Ile Thr Pro Glu Met Val Leu Pro Pro Met Lys Tyr Arg
                485                 490                 495

His Tyr Tyr Thr Tyr Glu Gly Ser Leu Thr Thr Pro Pro Cys Asn Glu
            500                 505                 510

Thr Val Leu Trp Val Val Glu Lys Cys His Val Gln Val Ser Arg Arg
        515                 520                 525

Val Leu Asp Ala Leu Arg Asn Val Glu Gly Tyr Glu Asp Gly Thr Thr
    530                 535                 540
```

```
Leu Ser Lys Tyr Gly Thr Arg Arg Pro Thr Gln Arg Asn Lys His Pro
545                 550                 555                 560

Leu Arg Val Tyr Lys Asn Ser Ile
                565

<210> SEQ ID NO 6
<211> LENGTH: 447
<212> TYPE: PRT
<213> ORGANISM: Pinctada fucata

<400> SEQUENCE: 6

Met Tyr Leu His Leu Thr Ala Leu Cys Val Ile Pro Leu Cys Tyr
 1               5                  10                  15

Gly Ala Ser Met Phe Lys His Asp His Tyr Met Asp Asn Gly Val Arg
                20                  25                  30

Tyr Pro Asn Gly Asp Gly Ile Cys Lys Gln Leu Asn Glu Thr Lys Cys
            35                  40                  45

Asp Ala Gly Phe Ser Tyr Asp Arg Ser Ile Cys Glu Gly Pro His Tyr
        50                  55                  60

Trp His Thr Ile Ser Lys Cys Phe Ile Ala Cys Gly Ile Gly Gln Arg
65                  70                  75                  80

Gln Ser Pro Ile Asn Ile Val Ser Tyr Asp Ala Lys Phe Arg Gln Arg
                85                  90                  95

Leu Pro Lys Leu Lys Phe Lys Pro His Met Glu Lys Leu Lys Thr Glu
            100                 105                 110

Val Thr Asn His Gln Asn Arg Ala Pro Glu Phe Glu Pro Glu Asp Gly
        115                 120                 125

Glu Asn Leu Tyr Val Lys Leu Asn Asn Leu Val Asp Gly His Tyr Lys
    130                 135                 140

Phe His Asn Leu His Val His Asn Gly Arg Thr Arg Arg Lys Gly Ser
145                 150                 155                 160

Glu His Ser Val Asn Gly Arg Phe Thr Pro Met Glu Ala His Leu Val
                165                 170                 175

Phe His His Asp Asp Gln Thr His Phe Glu Pro Thr Arg Thr Lys Leu
            180                 185                 190

Gly Gly Ala Phe Pro Gly His Asn Asp Phe Val Val Gly Val Phe
        195                 200                 205

Leu Glu Val Gly Asp Asp Gly Phe Gly Asp Glu Pro Asp Asp Glu Glu
    210                 215                 220

Cys Lys His Ile Leu Lys Gly His His Pro Asp Asn Asn Glu Asn Gly
225                 230                 235                 240

Asn Gly Asp Asn Gly Asn Asn Gly Tyr Asn Gly Asp Asn Gly Asn Asn
                245                 250                 255

Gly Asp Asn Gly Asn Asn Ser Tyr Asn Gly Asp Asn Gly Asn Asn Gly
            260                 265                 270

Val Asn Gly Asn Asn Gly Tyr Asn Gly Asp Asn Gly Asn Asn Gly Asp
        275                 280                 285

Asn Gly Asn Asn Gly Tyr Asn Gly Asp Asn Gly Asn Asn Gly Asp Asn
    290                 295                 300

Gly Asn Asn Gly Glu Asn Gly Asn Asn Gly Glu Asn Gly Asn Asn Gly
305                 310                 315                 320

Glu Asn Gly His Lys His Gly Cys Arg Val Lys Lys Ala Lys His Leu
                325                 330                 335

Ser Arg Ile Leu Glu Cys Ala Tyr Arg Asn Asp Lys Val Arg Glu Phe
```

-continued

```
                    340                 345                 350
Lys Lys Val Gly Glu Glu Gly Leu Asp Val His Leu Thr Pro Glu
            355                 360                 365

Met Ala Leu Pro Pro Leu Lys Tyr Arg His Tyr Tyr Thr Tyr Glu Gly
        370                 375                 380

Ser Leu Thr Thr Pro Pro Cys Thr Glu Ser Val Leu Trp Val Val Gln
385                 390                 395                 400

Lys Cys His Val Gln Val Ser Arg Arg Val Leu His Ala Leu Arg Asn
                405                 410                 415

Val Glu Gly Tyr Lys Asp Gly Thr Thr Leu Arg Lys Tyr Gly Thr Arg
            420                 425                 430

Arg Pro Thr Gln Lys Asn Lys Val Thr Val Tyr Lys Ser Phe Lys
        435                 440                 445
```